(12) United States Patent
Pasquino et al.

(10) Patent No.: US 11,672,552 B2
(45) Date of Patent: Jun. 13, 2023

(54) TRANSCATHETER DEVICE FOR THE TREATMENT OF CALCIFIED HEART VALVE LEAFLETS

(71) Applicant: AorticLab srl, Colleretto Giacosa (IT)

(72) Inventors: Enrico Pasquino, Savigny (CH); Francesco Bonetti, Chieri (IT); Franco Osta, Mombello-Monferrato (IT)

(73) Assignee: AorticLab srl, Colleretto Giacosa (IT)

( * ) Notice: Subject to any disclaimer, the term of this patent is extended or adjusted under 35 U.S.C. 154(b) by 267 days.

(21) Appl. No.: 16/645,830

(22) PCT Filed: Aug. 28, 2018

(86) PCT No.: PCT/IB2018/056553
§ 371 (c)(1),
(2) Date: Mar. 10, 2020

(87) PCT Pub. No.: WO2019/053538
PCT Pub. Date: Mar. 21, 2019

(65) Prior Publication Data
US 2020/0197033 A1    Jun. 25, 2020

(30) Foreign Application Priority Data

Sep. 12, 2017    (WO) .................. PCT/IB2017/055477

(51) Int. Cl.
*A61B 17/22*        (2006.01)
*A61B 17/3207*    (2006.01)
(Continued)

(52) U.S. Cl.
CPC .. *A61B 17/2202* (2013.01); *A61B 17/320725* (2013.01); *A61B 2017/00402* (2013.01);
(Continued)

(58) Field of Classification Search
CPC ...... A61B 2017/22098; A61B 17/2202; A61B 17/320725; A61B 17/22031;
(Continued)

(56) References Cited

U.S. PATENT DOCUMENTS 7,803,168 B2    9/2010    Gifford et al.
9,717,513 B2    8/2017    Golan
(Continued)

FOREIGN PATENT DOCUMENTS

WO    WO 2006/063199 A2    6/2006
WO    WO 2010/014515 A2    2/2010
(Continued)

OTHER PUBLICATIONS

International Search Report dated Dec. 7, 2018 for Patent Application PCT/IB2018/056553.
(Continued)

*Primary Examiner* — Kankindi Rwego
(74) *Attorney, Agent, or Firm* — Nixon & Vanderhye P.C.

(57) ABSTRACT

Transcatheter device for the treatment of calcified native heart valve leaflets comprising an outer hollow shaft (5), an inner hollow shaft (4) slidingly contained within said outer shaft (5) and an axle body (6) slidingly contained within said inner shaft (4); wherein the device comprises a commissure debridement system (7), located at the distal end of the axle
(Continued)

body (6), that is made of at least two radially expandable arms (7) that are adapted to be inserted in and aligned with native commissures.

7 Claims, 25 Drawing Sheets

(51) Int. Cl.
    *A61B 17/00*     (2006.01)
    *A61B 17/221*     (2006.01)
    *A61B 90/00*     (2016.01)
    *A61B 18/26*     (2006.01)

(52) U.S. Cl.
    CPC .............. *A61B 2017/22008* (2013.01); *A61B 2017/2212* (2013.01); *A61B 2017/22055* (2013.01); *A61B 2017/22062* (2013.01); *A61B 2017/22098* (2013.01); *A61B 2018/263* (2013.01); *A61B 2090/3966* (2016.02)

(58) Field of Classification Search
    CPC ............ A61B 17/22032; A61B 17/221; A61B 2017/00247; A61B 2017/22097; A61B 2017/22035; A61B 2017/2212; A61B 2017/2215; A61B 2017/00402; A61B 2017/22008; A61B 2017/22055; A61B 2017/22062; A61B 2090/3966; A61B 2018/263; A61F 2/2403; A61F 2/2406; A61F 2/2409; A61F 2/2421; A61F 2/2427; A61F 2/2433; A61F 2/2463; A61F 2/2466; A61F 2/95; A61F 2/962; A61F 2002/9528; A61F 2250/0003; A61M 25/10; A61M 25/1002; A61M 25/10181

USPC .................................................. 606/127, 128
See application file for complete search history.

(56) References Cited

U.S. PATENT DOCUMENTS

| | | | |
|---|---|---|---|
| 2002/0013571 A1* | 1/2002 | Goldfarb ............ | A61B 17/0625 606/1 |
| 2005/0075662 A1* | 4/2005 | Pedersen .............. | A61M 25/10 977/875 |
| 2007/0239141 A1* | 10/2007 | Hartley ................ | A61B 17/221 606/1 |
| 2008/0082107 A1* | 4/2008 | Miller .................. | A61B 17/221 606/127 |
| 2011/0118634 A1* | 5/2011 | Golan ............ | A61B 17/320725 601/4 |
| 2012/0253358 A1 | 10/2012 | Golan | |
| 2016/0135828 A1 | 5/2016 | Hawkins et al. | |
| 2017/0100159 A1 | 4/2017 | Pain et al. | |
| 2017/0119517 A1 | 5/2017 | Pain et al. | |
| 2018/0214165 A1* | 8/2018 | Golan .............. | A61B 17/22012 |
| 2020/0069421 A1 | 3/2020 | Pasquino et al. | |

FOREIGN PATENT DOCUMENTS

| | | |
|---|---|---|
| WO | WO 2011/069025 A1 | 6/2011 |
| WO | WO 2016/077627 A1 | 5/2016 |
| WO | WO 2020151995 | 7/2020 |
| WO | WO 2020201524 | 10/2020 |

OTHER PUBLICATIONS

International Written Opinion dated Dec. 7, 2018 for Patent Application PCT/IB2018/056553.

\* cited by examiner

TRANSCATHETER DEVICE FOR THE TREATMENT OF CALCIFIED HEART VALVE LEAFLETS

CROSS REFERENCE TO RELATED APPLICATIONS

The present application is a United States national stage application of International patent application PCT/IB2018/056553 filed on Aug. 28, 2018 that designated the United States, and claims foreign priority to International patent application PCT/IB2017/055477 filed on Sep. 12, 2017, the contents of both documents being herewith incorporated by reference in their entirety.

FIELD OF INVENTION

The invention relates to a transcatheter devices for the treatment of calcified heart valve leaflets, in particular aortic leaflets.

BACKGROUND

Aortic calcification, also called aortic sclerosis, is a buildup of calcium deposits on the aortic valve in the heart.

This often results in a heart murmur, which can easily be heard with a stethoscope over the heart. However, aortic calcification usually doesn't significantly affect the function of the aortic valve.

In some cases, though, the dystrophic calcium deposits thicken the leaflets and cause narrowing at the opening of the aortic valve. This impairs blood flow through the valve, causing dyspnea, chest pain or a heart attack. Doctors refer to such narrowing as aortic stenosis.

Aortic calcification typically affects older adults. But when it occurs in younger adults, it's often associated with an aortic valve defect (bicuspidia) that is present at birth associated with other illnesses such as kidney failure. A diagnostic ultrasound of the heart (echocardiography) can determine the severity of aortic calcification and also provide indications to the doctors about the need to proceed with a native valve replacement with valve prostheses. At present, there is no specific treatment for aortic valve calcification. General medical treatment includes the monitoring for further developments of heart disease. Cholesterol levels are also checked to determine the need for medications to lower cholesterol in the hope to prevent progression of native aortic valve calcification.

If the valve becomes severely narrowed, aortic valve replacement surgery may be necessary.

The aortic valve orifice area can be opened or enlarged with a balloon catheter (balloon valvuloplasty), which is introduced in much the same way as in cardiac catheterization.

With balloon valvuloplasty, the aortic valve area typically increases slightly. Patients with critical aortic stenosis can therefore experience temporary improvement with this procedure.

Unfortunately, most of these valves narrow over a six to 18-month period. Therefore, balloon valvuloplasty is useful as a short-term measure to temporarily relieve symptoms in patients who are not candidates for aortic valve replacement.

Patients who require urgent non-cardiac surgery, such as a hip replacement, may benefit from aortic valvuloplasty prior to surgery. Valvuloplasty improves heart function and the chances of surviving non-cardiac surgery. Aortic valvuloplasty can also be useful as a bridge to aortic valve replacement in elderly patients with poor ventricular function. Balloon valvuloplasty may temporarily improve ventricular muscle function, and thus improve mid-term survival.

Those who respond to valvuloplasty with improvement in ventricular function can be expected to benefit even more from aortic valve replacement. Aortic valvuloplasty in these high-risk elderly patients has a similar mortality (5%) and serious complication rate (5%) as aortic valve replacement in surgical candidates.

Despite this data the balloon valvuloplasty alone is not anymore performed since its clinical results are not stable in the time. The action of the valvuloplasty balloon is coarse and mainly acting on the valve's commissures. The increase of geometric orifice area is mainly due to a mechanical dilation and no calcium debridement occurs in fact the leaflets remain stiff.

Nowadays the balloon valvuloplasty is still extensively used in association to all transcatheter aortic valve implant procedures (TAVI). It is intended as preparatory procedure in order to optimize the deployment of the self-expandable or balloon expandable bioprostheses. The preparatory work of the valvuloplasty is to mechanically increase the orifice area. Nonetheless, very often the leaflet calcification grade is asymmetric and the valvuloplasty doesn't leave an even orifice. Therefore, TAVI deployment can result suboptimal. The principal clinical consequence of this is a remarkable incidence of paravalvular leakages.

GENERAL DESCRIPTION OF THE INVENTION

The present invention, as defined in the claims, provides an alternative treatment system for stenotic and calcified aortic valves. As will be seen subsequently, the embodiments described herein provide a fine and more tolerable treatment of calcified aortic valves than the currently performed aortic valve replacement.

The device object of this invention intends providing a treatment of the stenotic aortic valve far more effective and durable than the balloon valvuloplasty.

The device of the invention is able to provide a selective calcium debridement from calcified native valve leaflets. One active portion of the device in fact is designed to restore the valve commissures that are often fused as a consequence of a pathologic dystrophic calcification narrowing the valve orifice. In a preferred embodiment of the invention, a second active portion of the device is devoted to embrace or to pinch each native leaflet, e.g. from the inflow (ventricular) and outflow (aortic) sides in order to perform a calcium debridement by fragmentation of the calcific vegetations present on the leaflets' surface.

The debridement procedure of the native valve is preferably based on the application of one or more energy sources used alone or combined. Advantageously the device may generate, localized cavitation phenomena able to wear and fragment extrinsic calcific formations making the native valve leaflets, at the end of the procedure, more pliable with an increased orifice area, lower transvalvular pressure gradients and consequently a better quality of life for the patient. Where appropriate a flow of micro-bubbles of carbon dioxide ($CO_2$) or other biocompatible gases is generated by the device structures in order to magnify the cavitation activity.

DETAILED DESCRIPTION OF THE INVENTION

The invention will be better understood below with illustrated examples that all refer to the treatment of aortic valves.

The invention is of course not limited to those examples.

NUMERICAL REFERENCES USED IN THE FIGURES

1-Guidewire.
2-Distal tip of the device.
3-Dystrophic calcification present on the leaflet and on the aortic root inner wall (Valsalva bulges).
4-Inner hollow shaft of device.
5-Outer hollow shaft of device.
6-Metallic axle body that contains the guidewire 1.
7-Commissural dilators and debriders integrated into the axle body 6. Three arms placed at 120° carrying on blades placed outwards.
8-Aortic leaflet supports. Three arms placed at 120°.
9-Aortic leaflet debriders. Three arms placed at 120°.
10-Debrider arms. Normally are two arms (wires or pipes) for each leaflet creating specific geometries adapting inside the leaflets' bellies.
11-Micro-piezoelectric elements loaded over the debrider arms 10.
12-Micro-holes in commissural debriders 7 or in aortic leaflet debrider arms 9 (embodiment with pipes) conveying $CO_2$ gas.
13-Micro-incisions on the debrider arm 10 surface providing flexibility and better adaptation to the leaflet's belly. The incisions must be superficial without cutting the entire thickness of the pipe.
14-External pipe of the debrider arm 10. This layer can be connected to a positive or negative charge.
15-Intermediate layer of the debrider arm 10 characterized by a piezoelectric material (ceramic, polymeric, etc.)
16-Internal pipe of the debrider arm 10. This layer can be connected to a positive or negative charge.
17-Internal lumen of internal pipe 16. Inside this lumen can circulate cooling liquid (e.g. water) or a cooling gas (e.g. $CO_2$) avoiding, if needed, an excessive increase of temperature during the procedure.
18-Micro-piezoelectric elements loaded on the debrider balloons and their relative electric connections.
19-Debrider balloons carrying piezoelectric elements.

PROCEDURE

The debridement procedure of dystrophic calcific formations on the native leaflets is obtained releasing energy to the calcified leaflets so that is inducing a localized cavitation condition. The cavitation phenomenon generates vapor micro-bubbles. The implosion of the generated micro-bubbles is releasing a great quantity of kinetic energy able to crack the calcific nodules and vegetations. The result should be an increased valve orifice area, leaflet pliability and therefore lower pressure gradients with an improved clinical condition for the patients.

Figure 1:
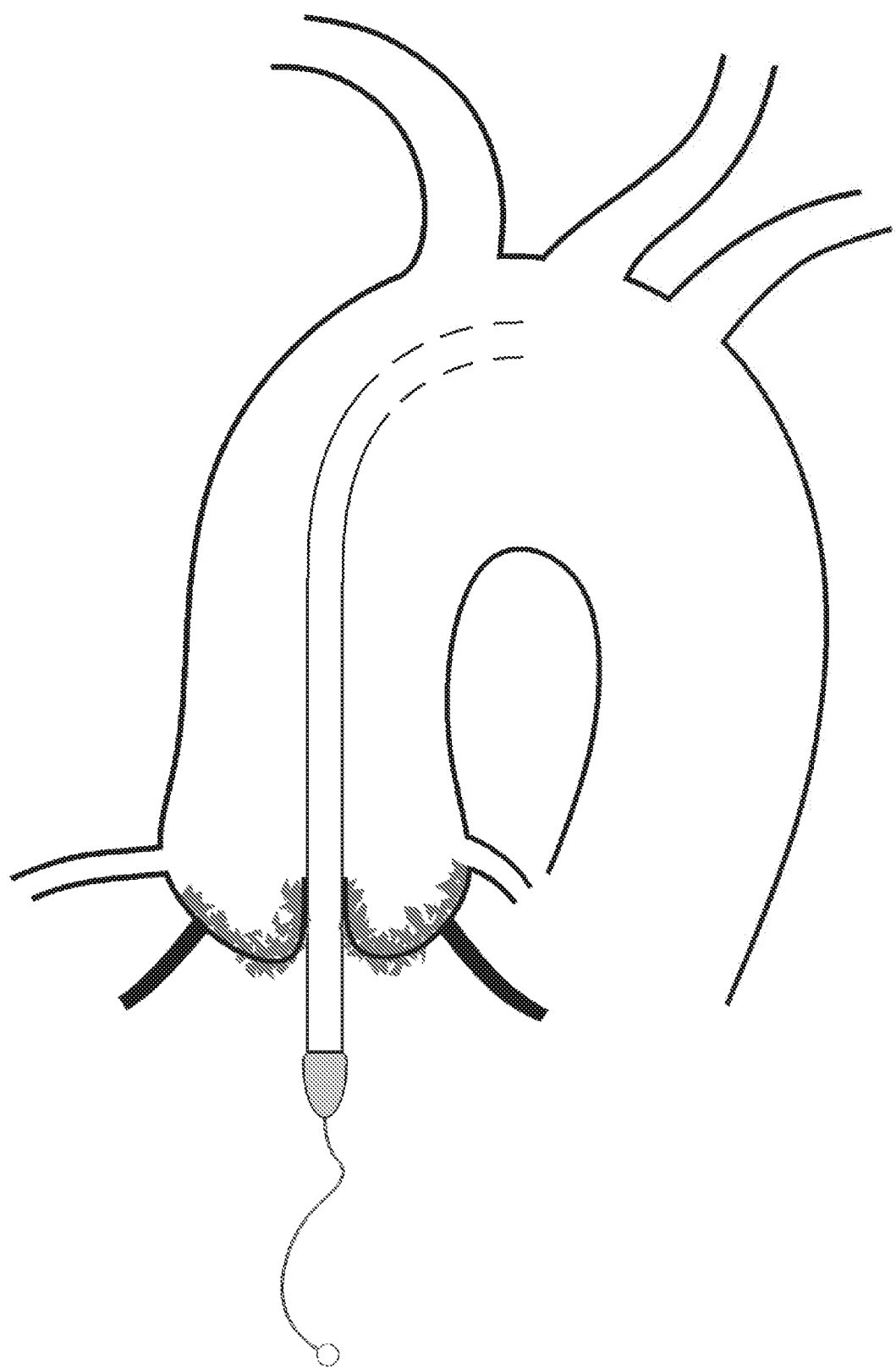
FIG. 1: aortic root with a stenotic calcified native valve. The calcific vegetations 3 are mainly present on the aortic side of the native leaflets and infiltrating the aortic root.

The device is inserted adopting a consolidated interventional procedure based on the puncture of the femoral artery. The device is pushed forward, over a guidewire previously positioned, into the arterial blood stream till reaching the ascending aorta and crossing the native aortic valve (FIG. 1).

Figure 2:
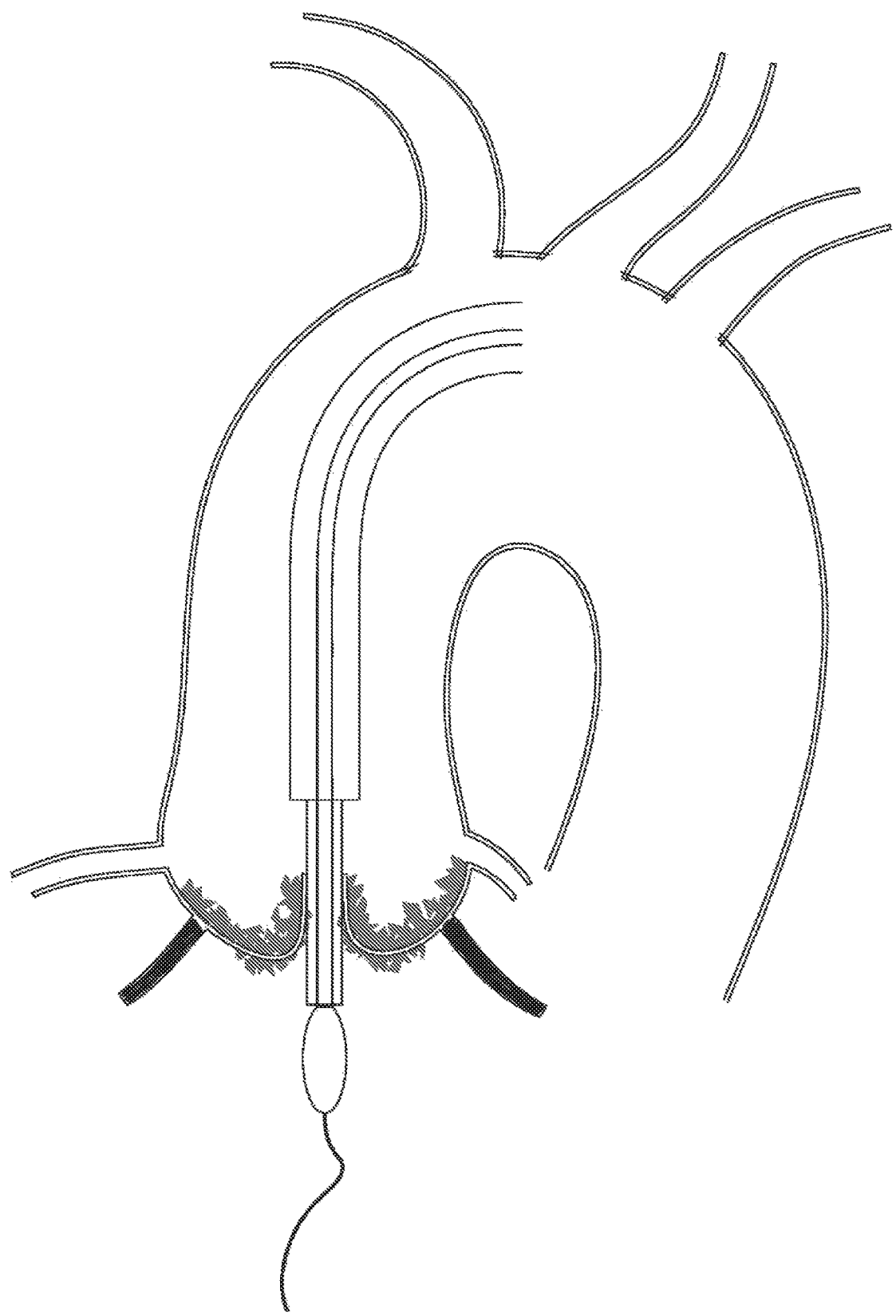
FIG. 2: after positioning a guidewire 1 through the native valve the inner hollow shaft of the device 4 is placed across the valve.
Figure 3:
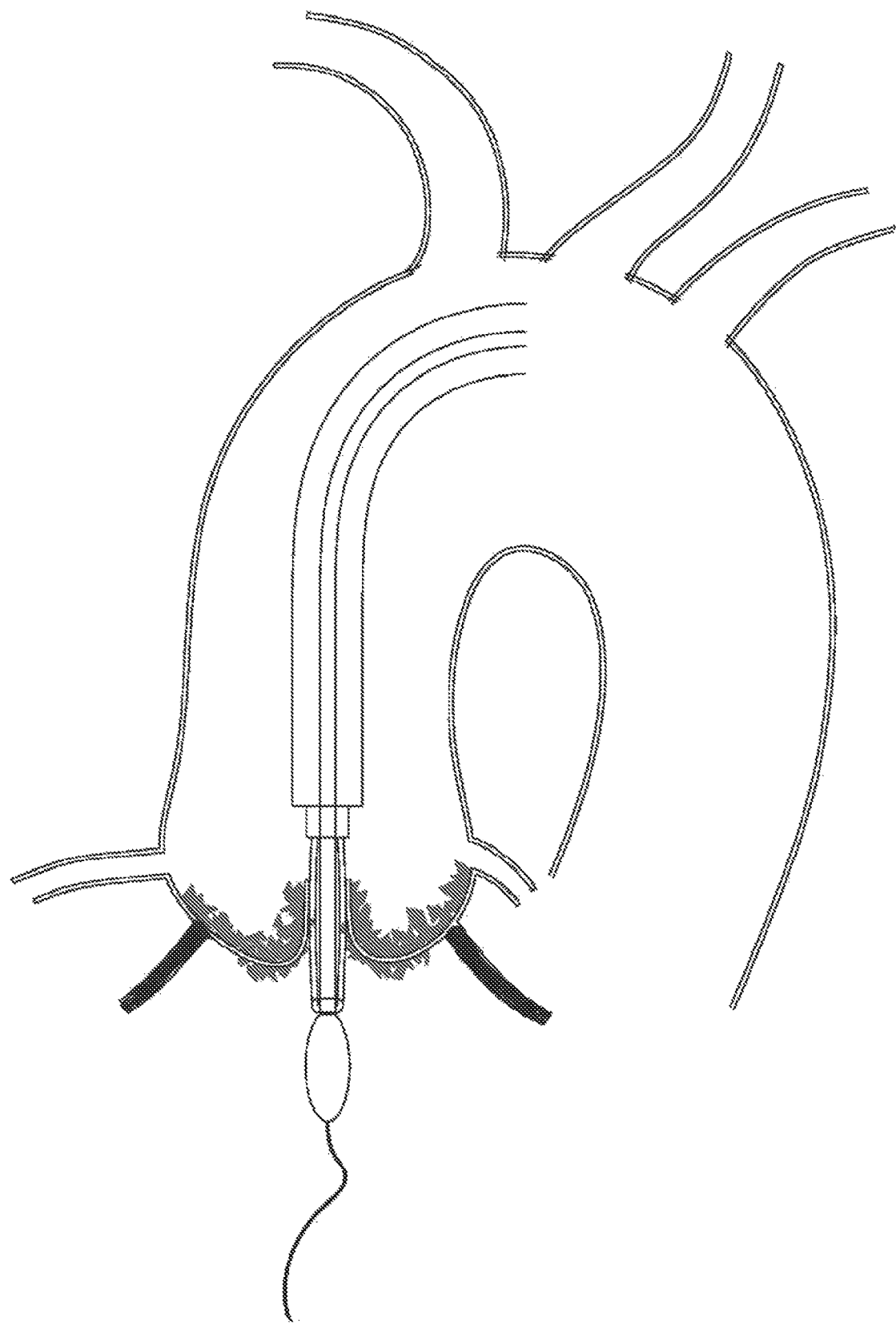
FIG. 3: the inner hollow shaft 4 is partially retracted inside the outer hollow shaft 5 and the commissural dilator and debrider 7 is exposed.

The outer hollow shaft 5 of the device is retracted exposing the inner hollow shaft 4 (FIG. 2). The inner hollow shaft 4 is also retracted exposing the structure of the commissural debrider 7 part of the axle body 6 (FIG. 3).

Figure 4:
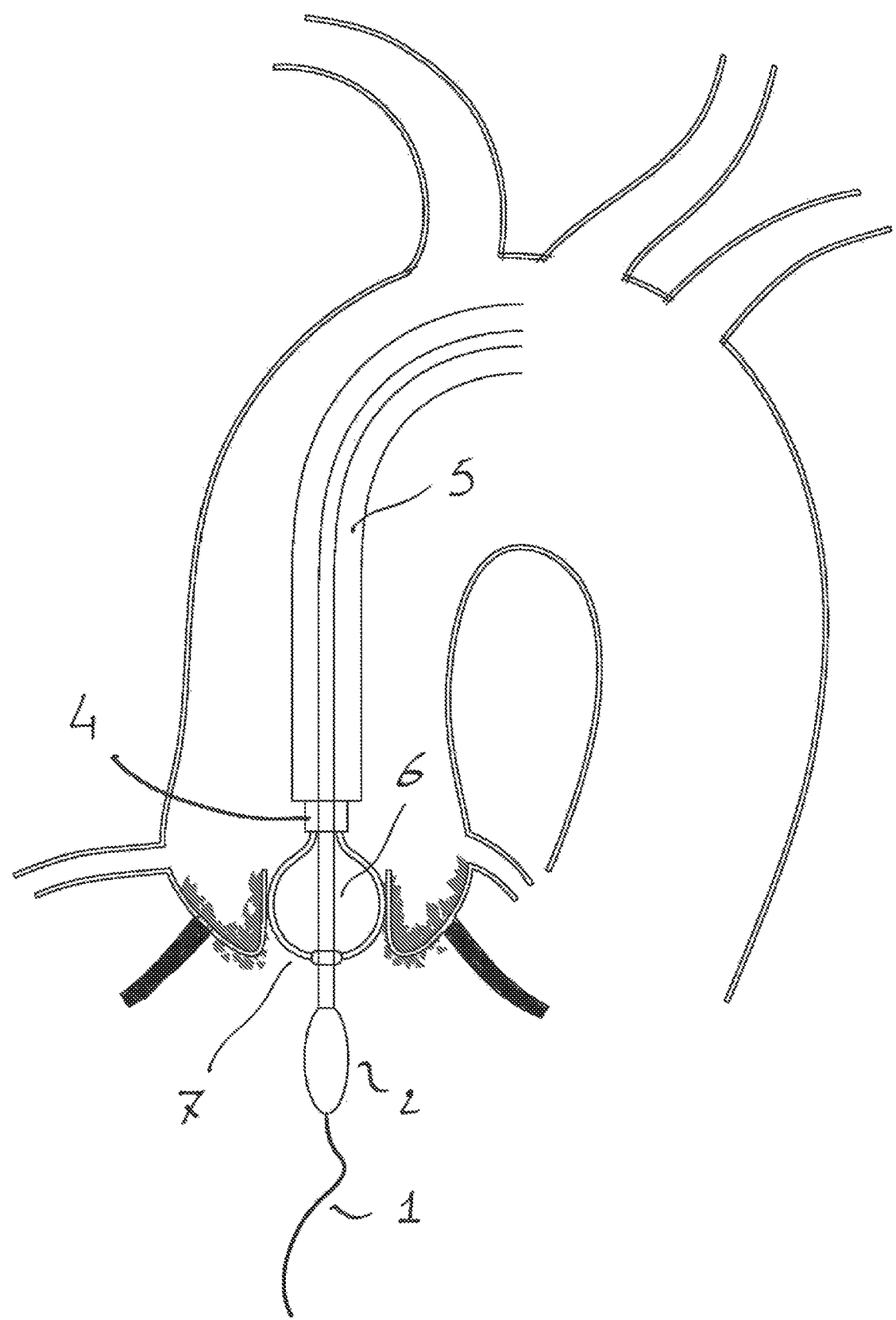
FIG. 4: The commissural debriders 7 with three arms at 120° is opened.
Figure 9:
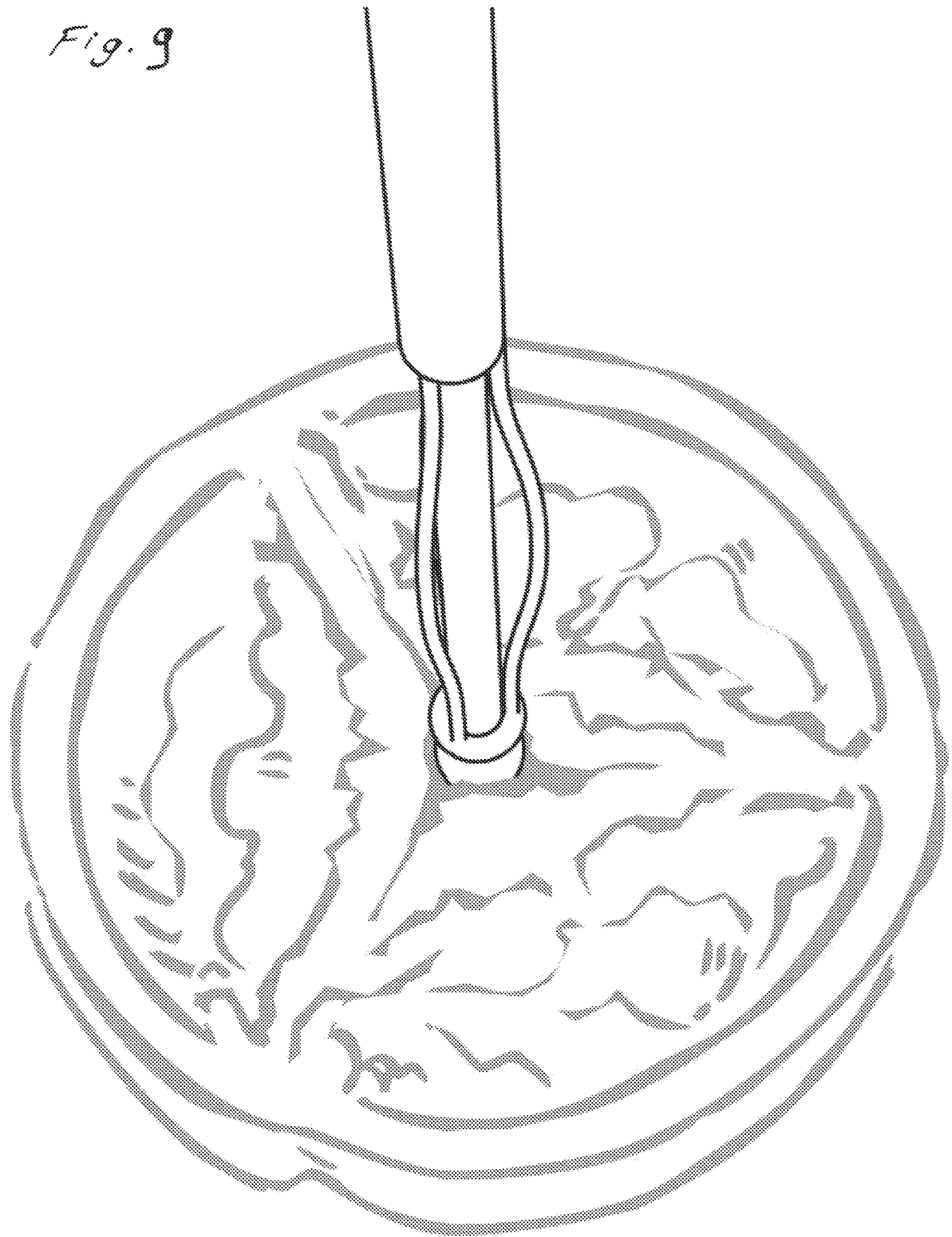
FIG. 9: The device is positioned inside the stenotic aortic valve. The commissural debriders 7 are still in closed position.
Figure 10:
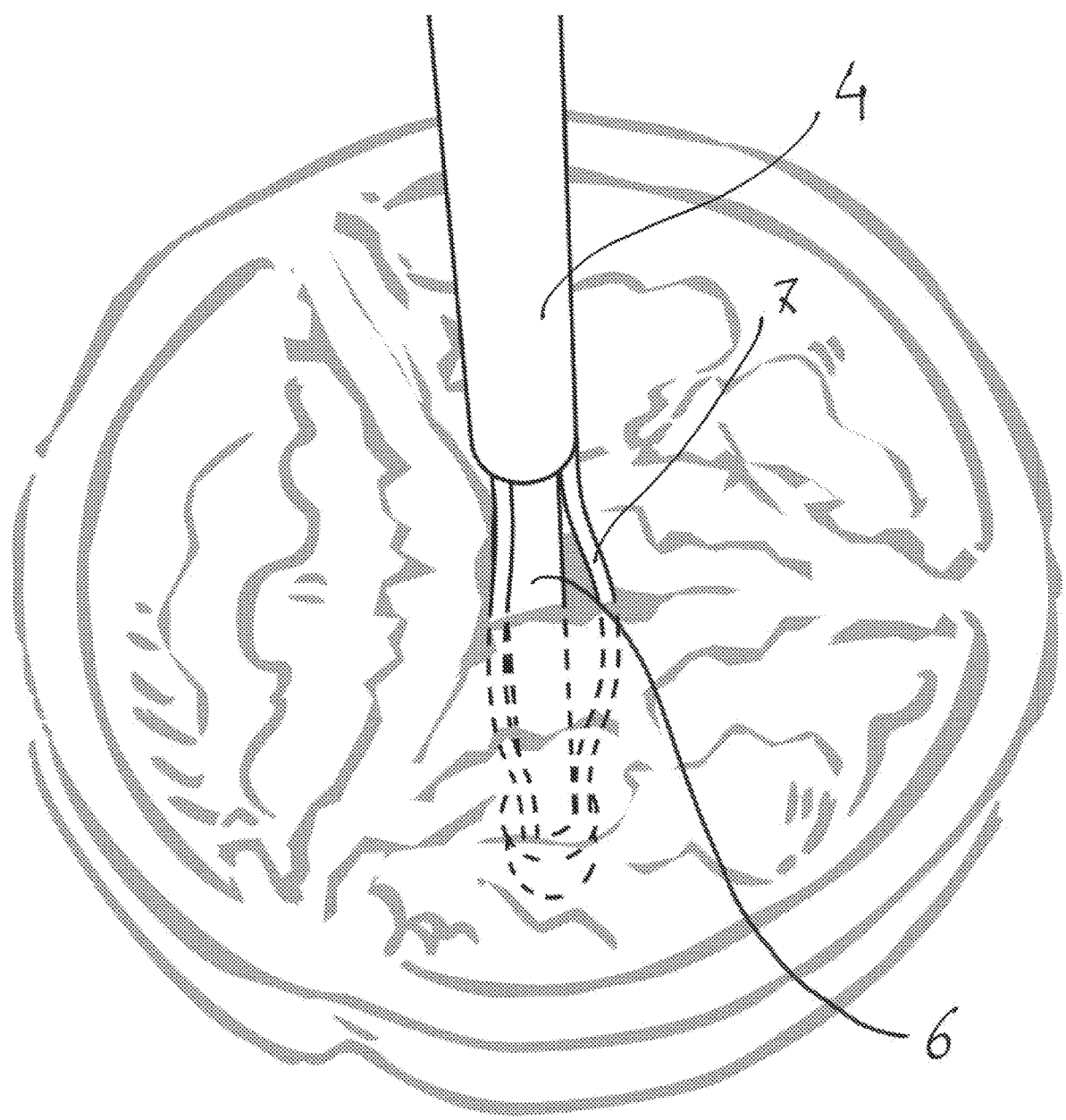
FIG. 10: The commissural debriders 7 are oriented/rotated by 3D echocardiographic guidance to get aligned with native commissures of the valve.
Figure 11:
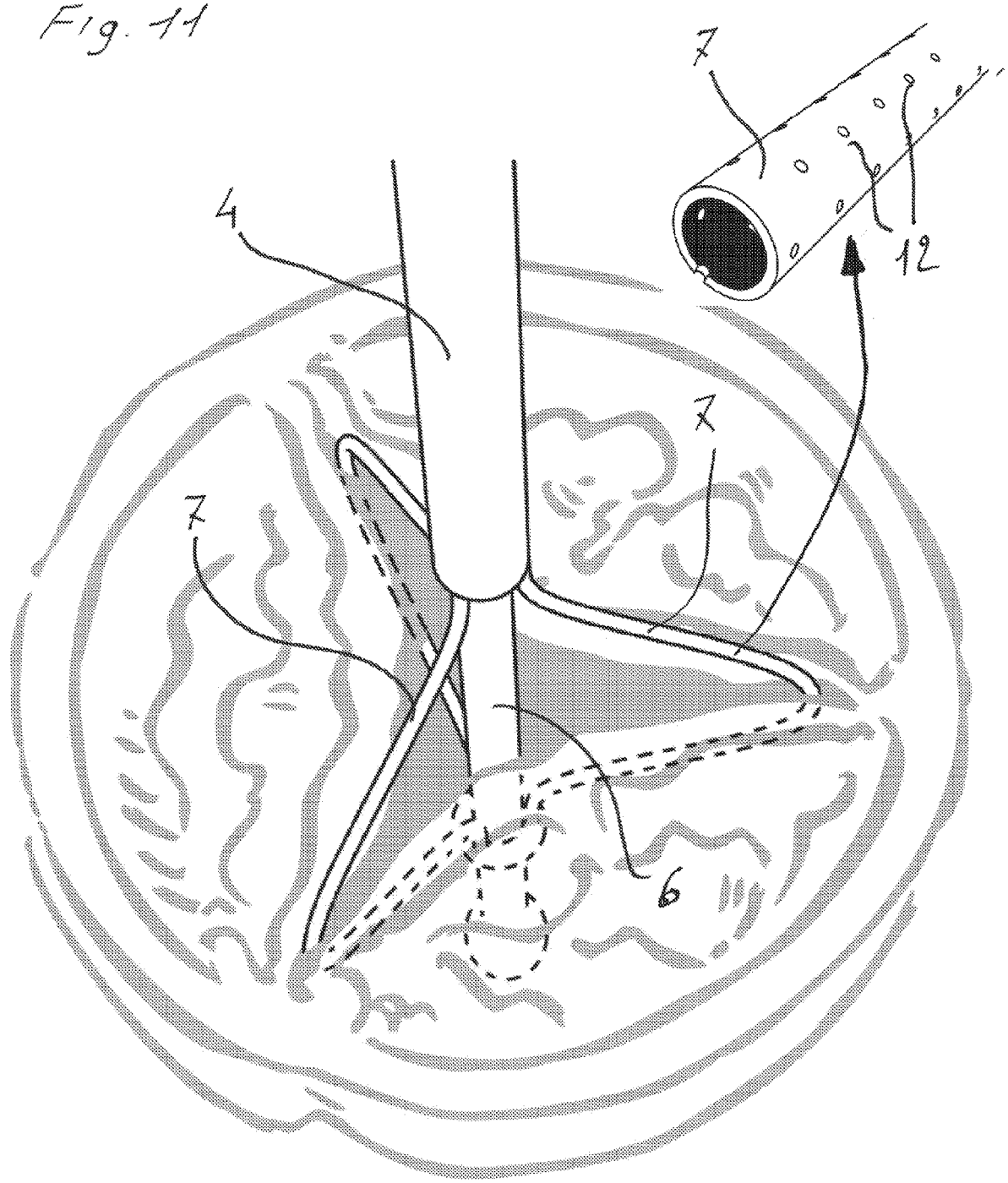
FIG. 11: The commissural debriders 7 are opened. The function is to find a cleavage that will debride the native fibrotic commissures fused by calcific deposits.

At this stage, the commissural debrider 7 is expanded and the native valve is dilated (FIG. 4). The three arms of the debrider, placed at 120°, tend to re-open the calcified commissures thanks to the mechanical action and to the energy delivered by the debrider to the tissue (FIGS. 9, 10, 11). In this embodiment, an example of preferred energy source could be the radiofrequency associated with emission of $CO_2$ micro-bubbles but also other energy sources could be suitable for such purpose.

Figure 5:
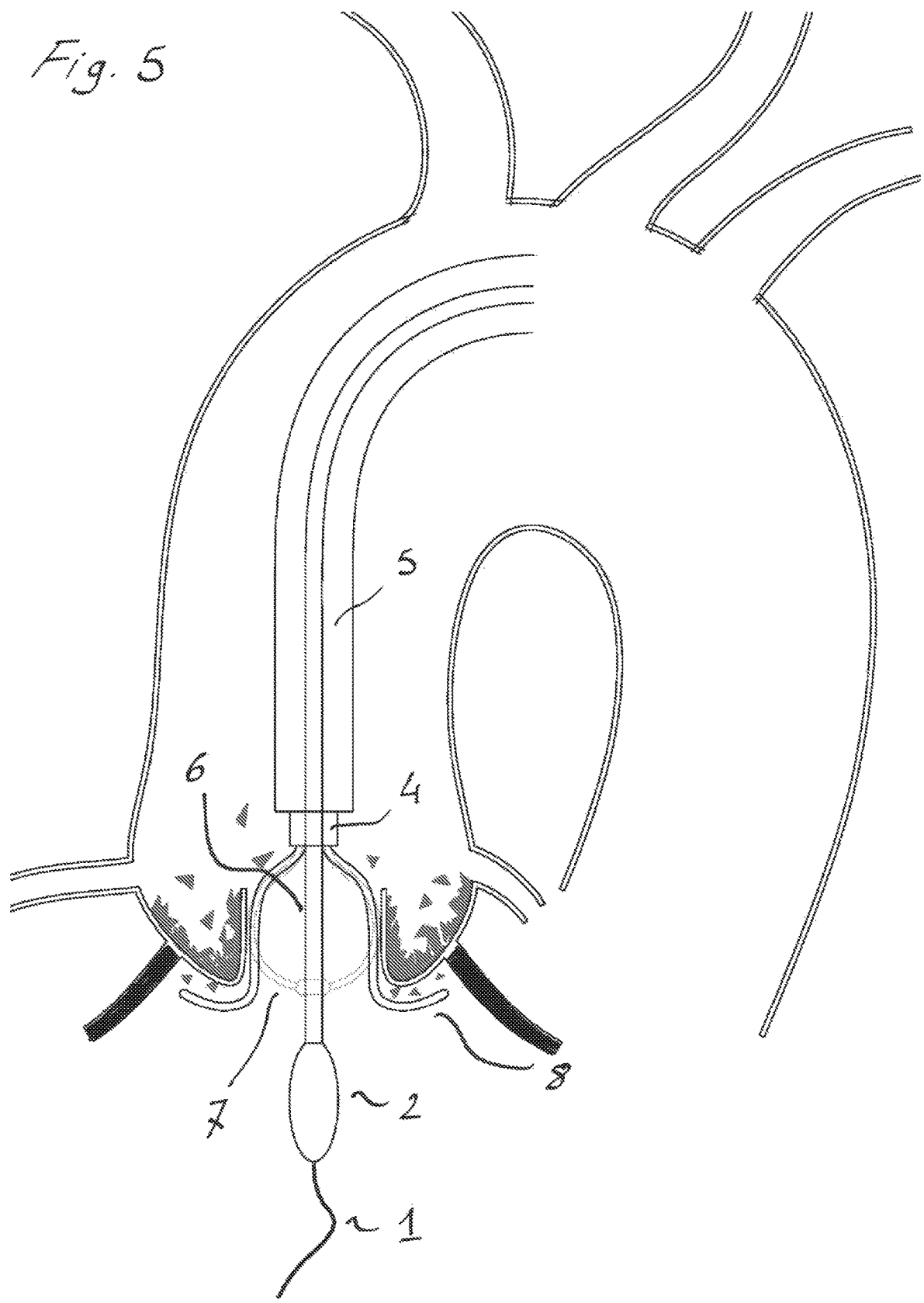
FIG. 5: Three aortic leaflet supports 8 are opened from the inner hollow shaft 4. They have the function to sustain the leaflets during the debridement procedure.

The aortic leaflet supports 8 are then extracted from the inner hollow shaft 4 (FIG. 5) and positioned below, and in correspondence of the native leaflets with the intent to sustain them during the procedure.

Figure 6:
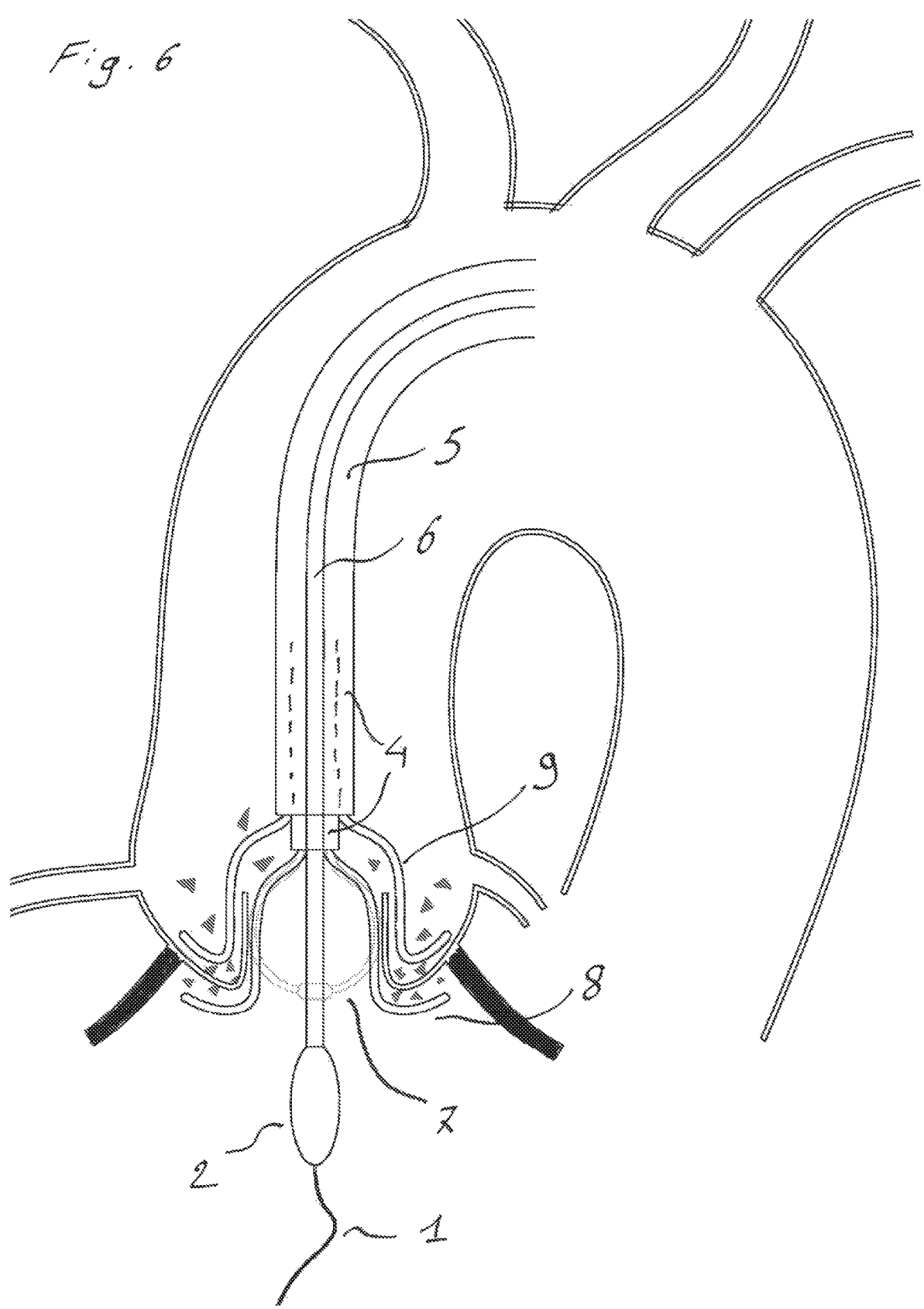
FIG. 6: Three aortic leaflet debriders 9 are opened from the outer hollow shaft 5. They have the function of active debridement of the calcific deposits present on the native valve leaflets.

In FIG. 6 the aortic leaflet debriders 9, contained in the gap between the inner hollow shaft 4 and the outer hollow shaft 5, are extracted and positioned in the belly of calcified leaflets.

Figure 21:
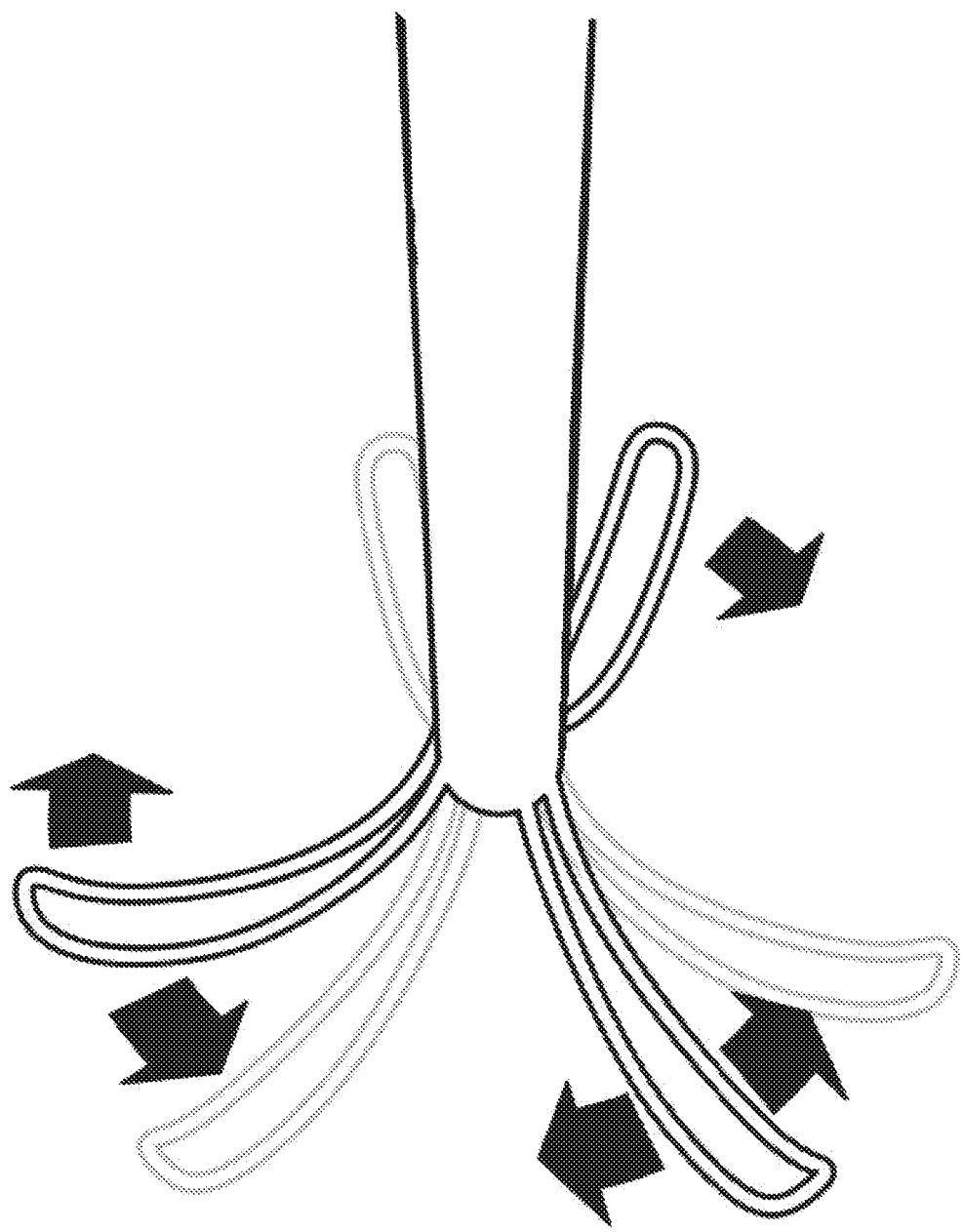
FIG. 21: The swiveling mechanism is represented. The motion of the debriders' arms 10 is aimed at maximizing the debridement effect created by the cavitation.

The debridement procedure is therefore performed (FIG. 6) while the commissural debrider 7 is open. In order to obtain a better effect treatment, in breaking the calcific nodules and vegetations, a swirling movement of the leaflet debriders 9 should be performed (FIG. 21). The debridement procedure lasts for several minutes (approximately from 1 to 15-20 minutes) and in the meanwhile the native valve stays in open position creating a significant problem of insufficiency and a risk of debris embolization. In order to overcome this critical hemodynamic condition a temporary valve function and an embolic filter protection should be foreseen.

Figure 7:
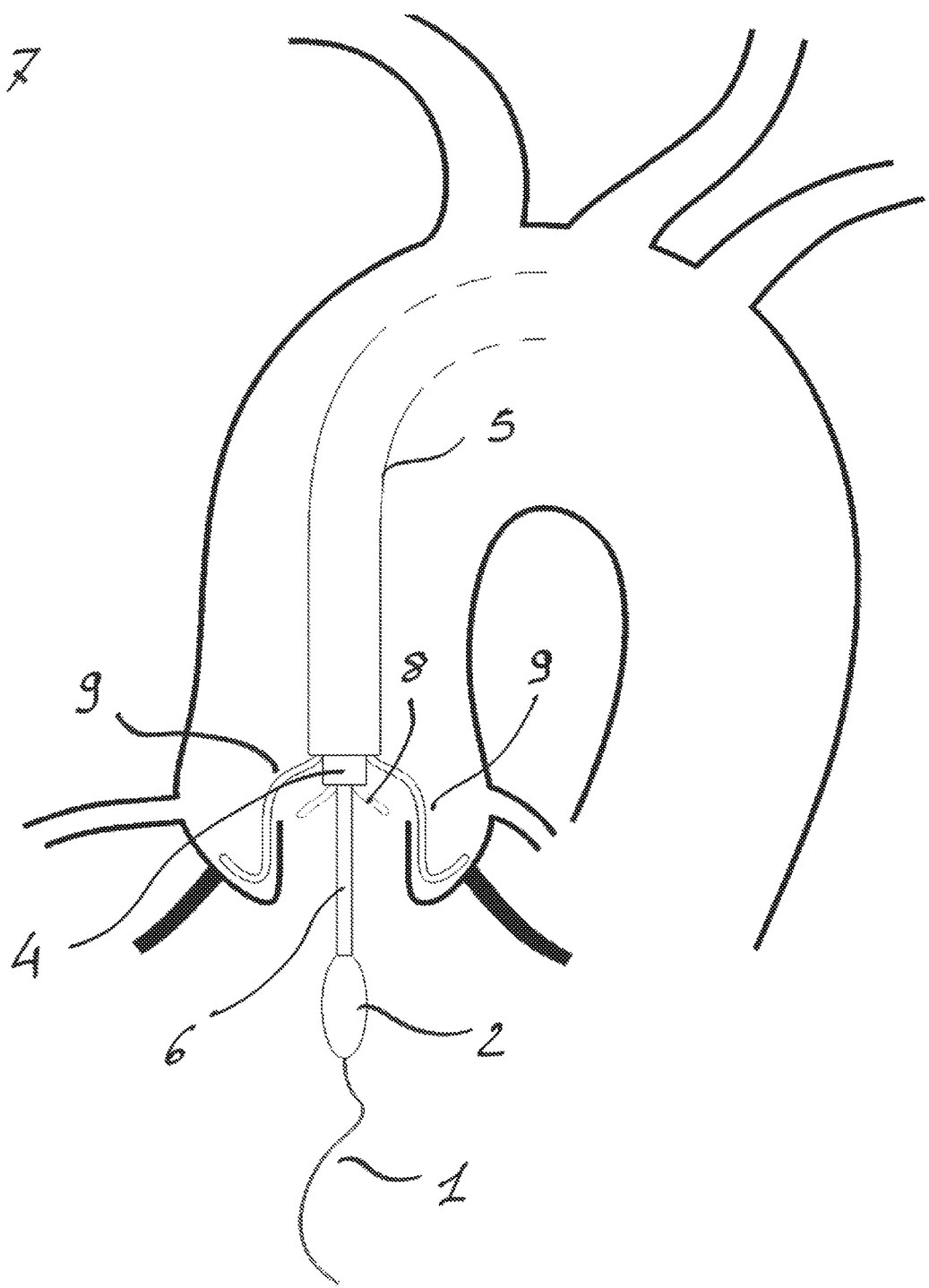
FIG. 7: The aortic leaflet supports 8 are being retracted into the gap between the inner hollow shaft 4 and the axle body 6.

At the end of the procedure the commissural debriders 7 are closed in the wall of the axel body 6 and the aortic leaflet supports 8 are retracted inside the inner hollow shaft 4 (FIG. 7).

Figure 8:
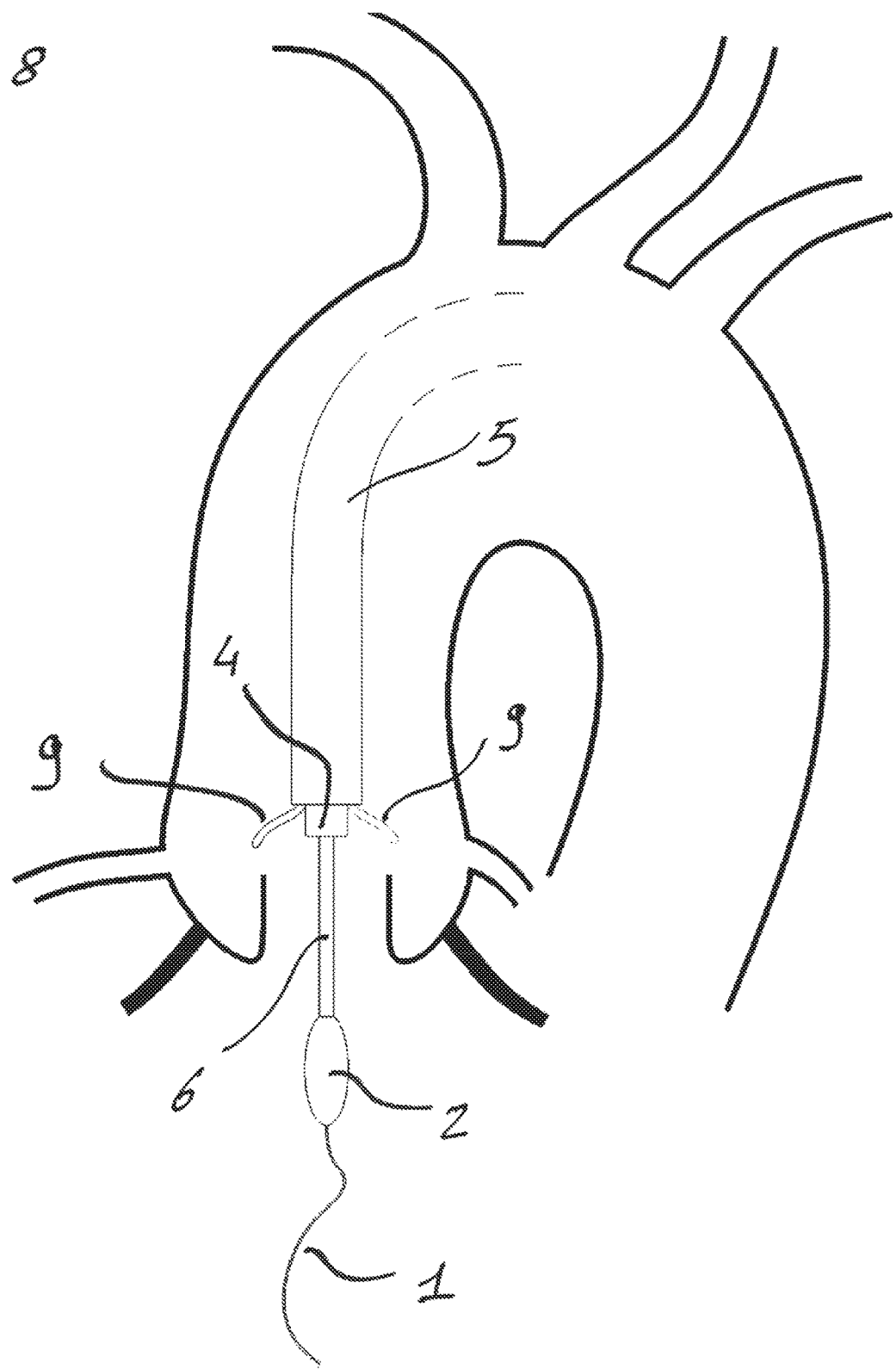
FIG. 8: The aortic leaflet debriders 9 are being retracted in the gap between the outer hollow shaft 5 and the inner hollow shaft 4.

Subsequently as described in FIG. 8, also the aortic leaflet debriders 9 are retracted inside the outer hollow shaft 5.

The final operation is the advancement of the outer hollow shaft 5 until reaching the tip 2 obtaining the complete closure of the device. The device together with the guidewire 1 are then retrieved out from the artery of the patient.

DETAILED DESCRIPTION OF THE INVENTION

This debridement device has two main functions that could be applied independently. The first one consists in re-opening the native commissures of the valve while the second one is aimed at returning certain pliability to the native calcified leaflets.

The commissural debridement procedure is definitely important in particular in complex TAVI procedure where the aortic valve commissural fusion is huge. In these cases, deploying the TAVI, without re-opening the commissures and/or making the leaflets more pliable, represents a high risk of prosthetic asymmetry with consequent one or more lazy leaflets and perivalvular leaks.

The debridement procedure at commissures is obtained applying a mechanical action with the three commissural debriders 7 place at approximately 120°. Three blades positioned on the outer surface of the commissural debriders 7 can provide an initial cutting mechanical action. The cutting action (constant pressure or pulsed at high frequency) in order to be completely effective should be associated with another energy source such as preferably, but not exhaustively, the radiofrequency with or without the presence of $CO_2$. The combined cutting and radiofrequency or ultrasound actions with $CO_2$ should maximize the debridement effect on the commissure obtaining a cavitation condition. The cavitation effect is maximized when an electromagnetic energy source is combined with $CO_2$ so that a great number of micro-bubbles implode freeing impact waves eroding the calcified tissues. The commissural debridement is described in more details in FIGS. 9, 10, 11. The injection of liquid $CO_2$ has also the effect of cooling down the commissural debriders 7 avoiding overheating of the tissues.

In another example the three commissural debriders 7 blades, placed outwards towards the calcified tissues, could deliver localized high-pressure micro-jets of saline with the aim of making the debridement action, on mineralized tissues, more aggressive.

In another example, the three commissural debriders 7 could be realized with laser fibers at lateral diffusion. Also in this case the emission of a laser beam is creating a cavitation condition that could be associated with the emission of $CO_2$ micro-bubbles with the scope of potentiating the erosion effect on the calcified leaflet tissues.

Another important objective of this inventive concept is to restore the leaflets' pliability with the aim to optimize a TAVI implant as well as providing a palliative improvement of the aortic valve function in patients without indication for TAVI.

The embodiments above described for the commissural debriders 7 are largely applicable to the aortic leaflet debriders 9 and their debrider arms 10.

With exception of the discouraged blades' application too dangerous for this debridement function the other embodiments are fully applicable.

Figure 12:
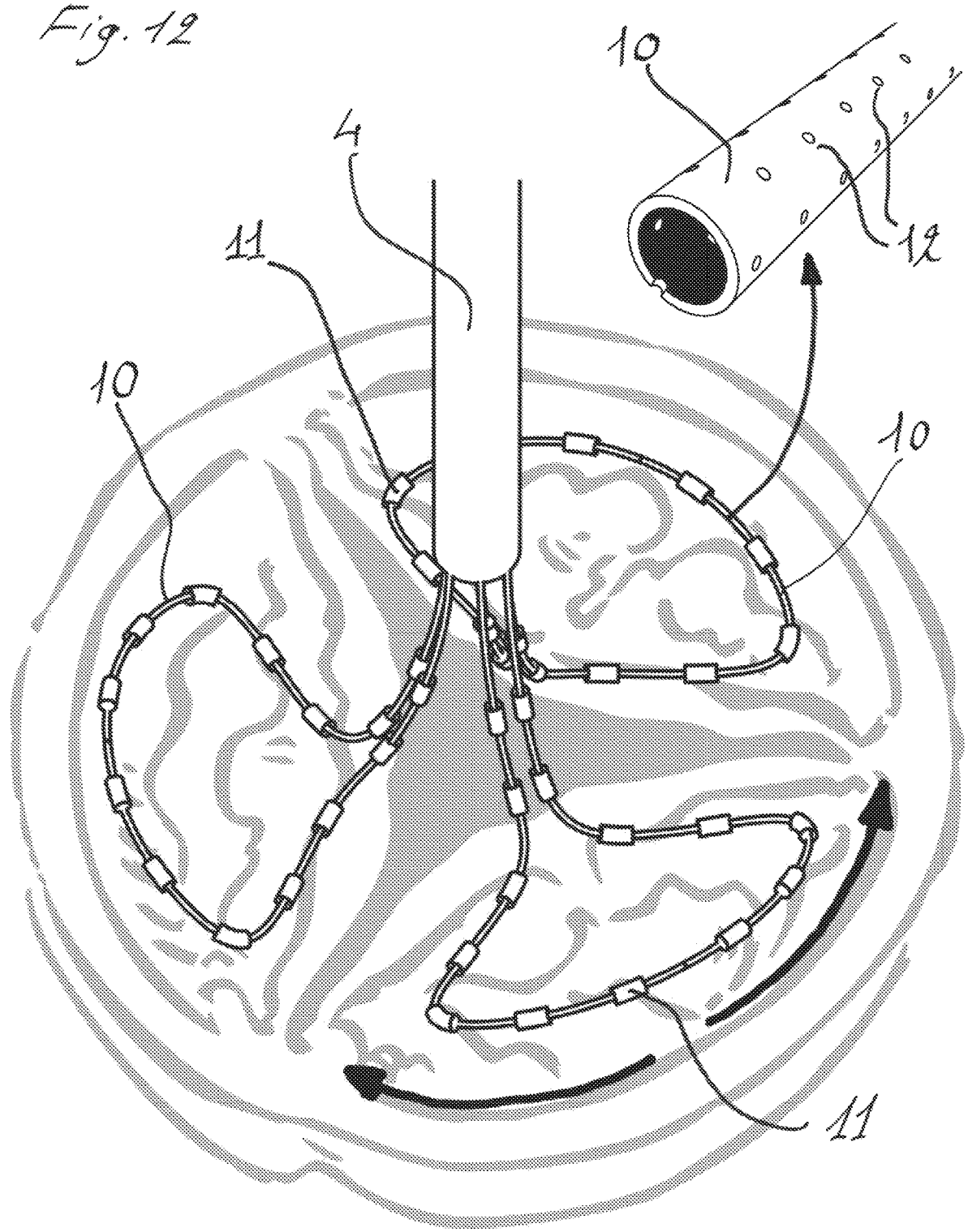
FIG. 12: The aortic leaflet debriders 9 are opened out from the outer hollow shaft 5. The three-aortic leaflet debriders 9 are designed to seat inside the belly of the native leaflets and get in contact with calcified tissues. The action mechanism is based on delivering an energy source so that a cavitation condition is obtained. In the present embodiment, the debriders' arms are carrying on micro-piezoelectric elements 11. The debrider arms 10 are loaded with micro-piezoelectric cylinders or plates. The same debrider arms can be a wire or a pipe with micro-holes conveying $CO_2$ gas in order to amplify the calcific tissue erosion mechanism by cavitation.
Figure 13:
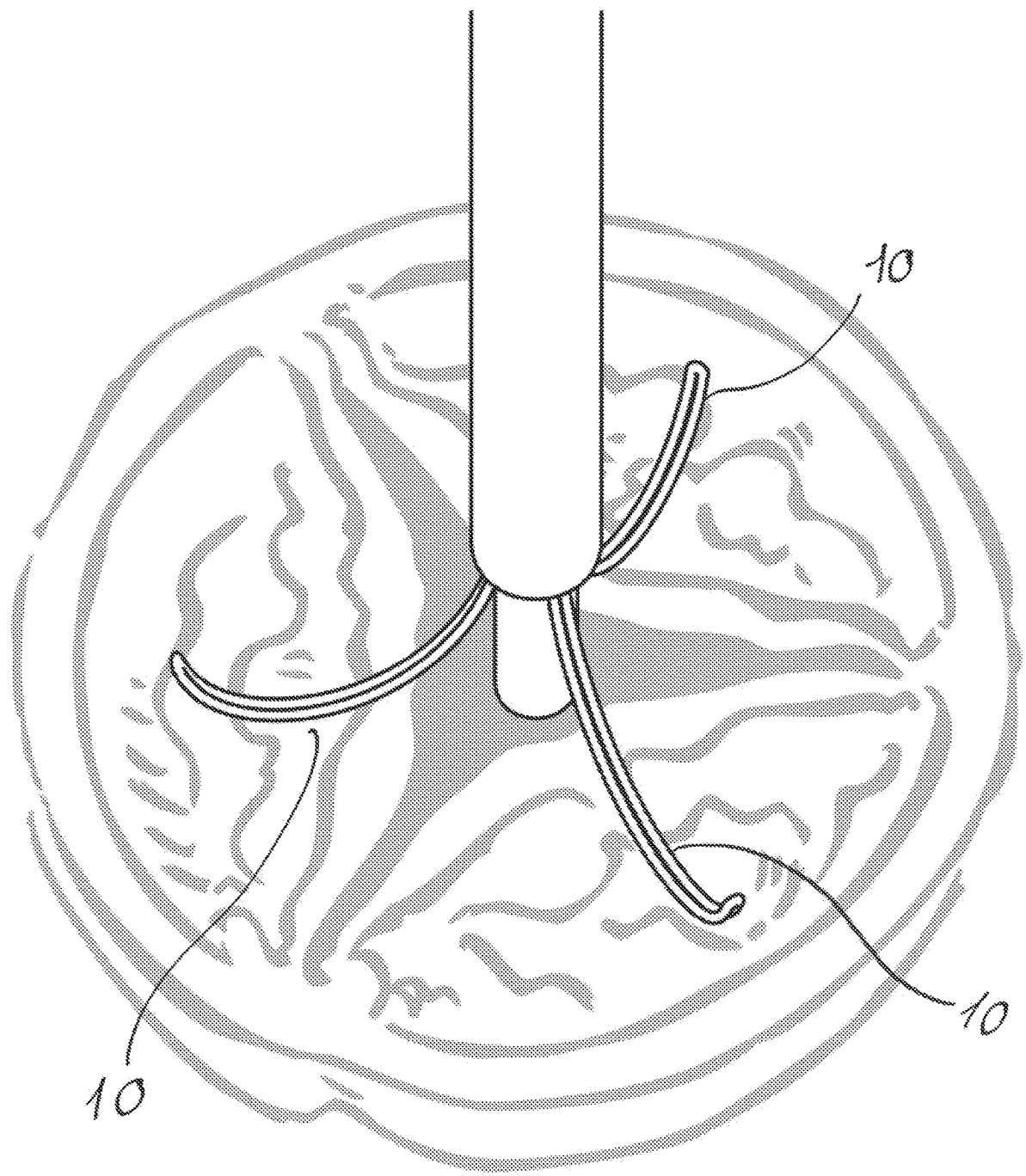
FIGS. 13, 14, 15, 16, 17, 18, 19, and 20 show different embodiments of the geometric configurations of the debrider arms 10. The other components of the device have been omitted for simplicity of visualization.
Figure 14:
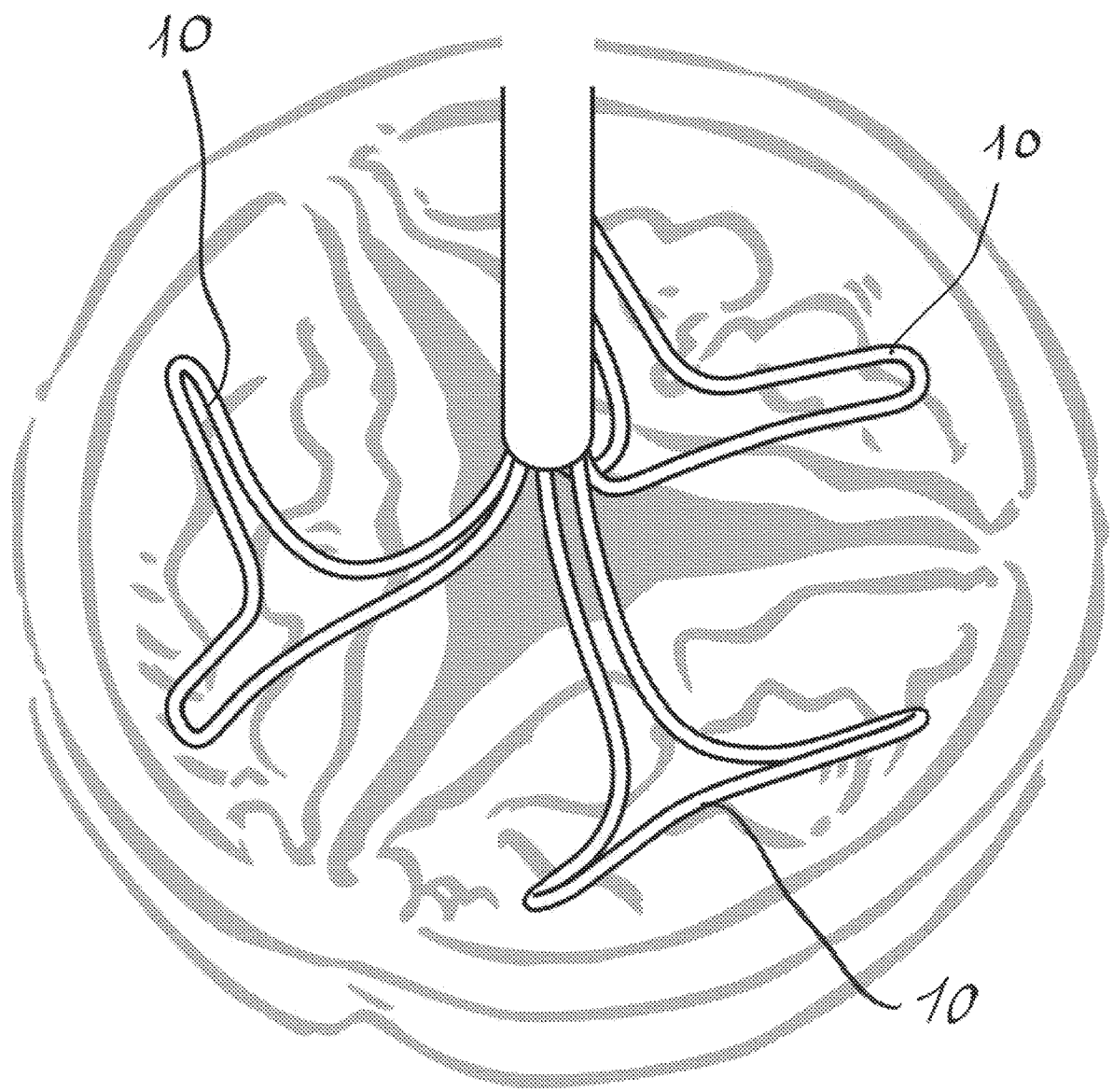
Figure 15:
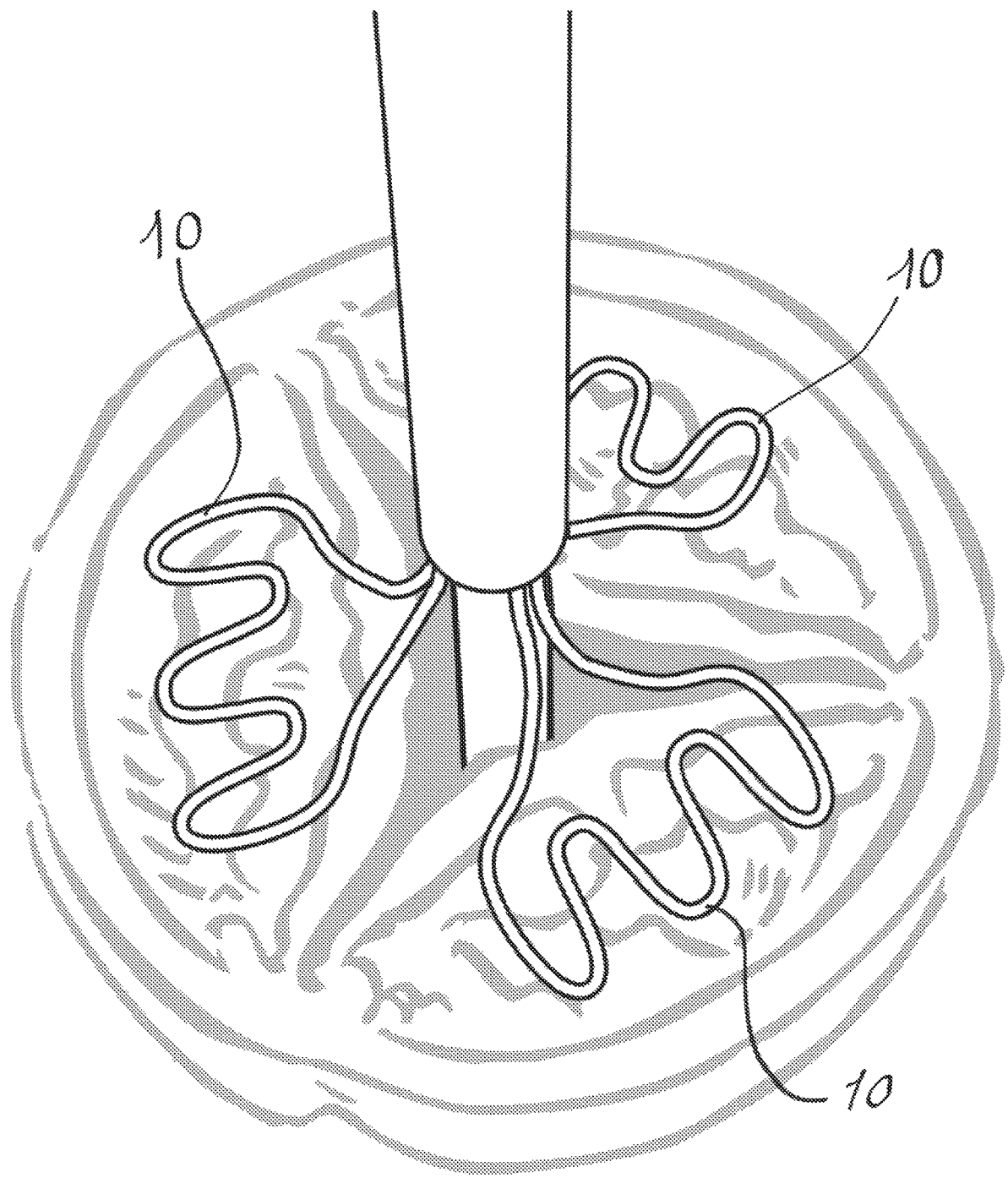
Figure 16:
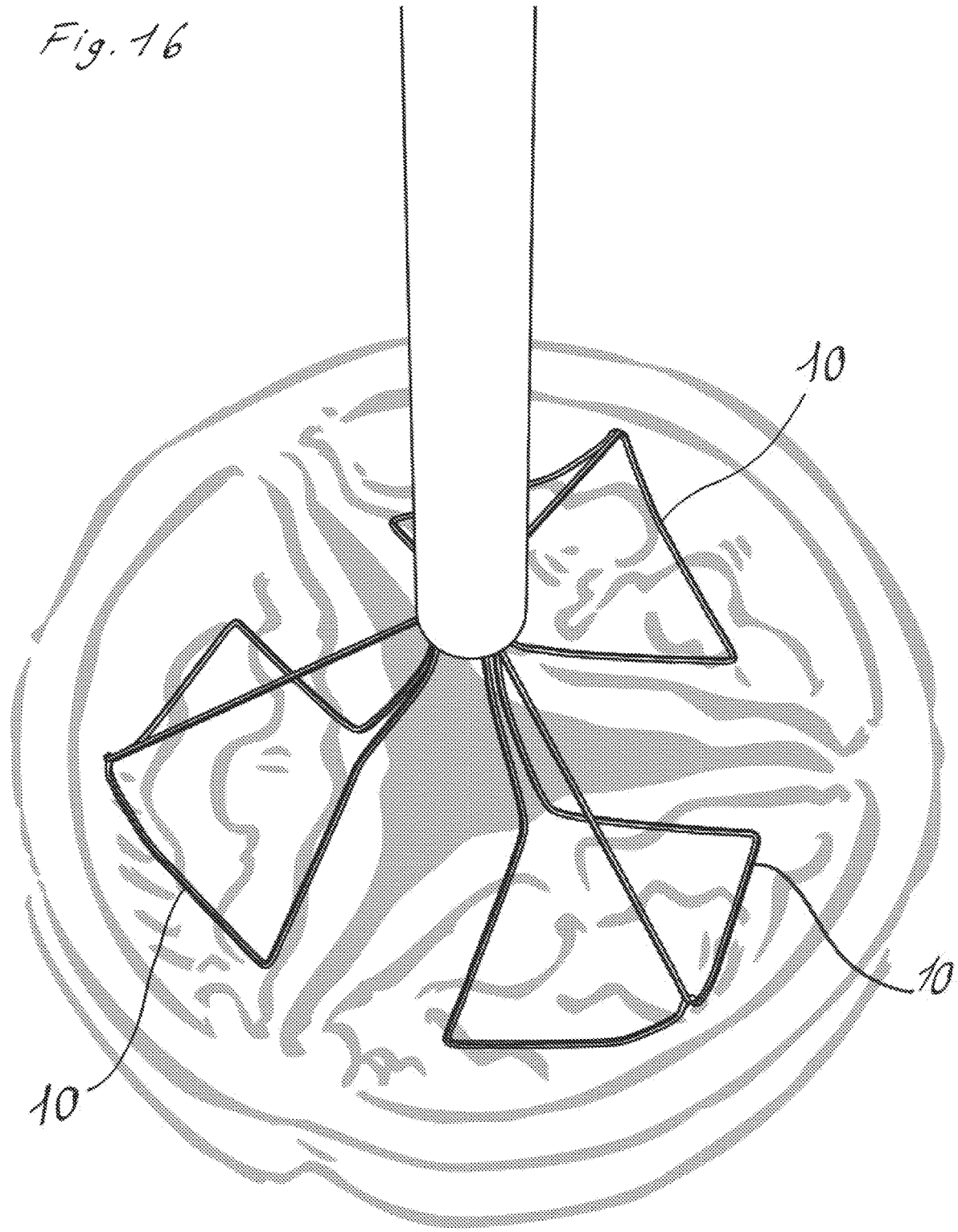
Figure 17:
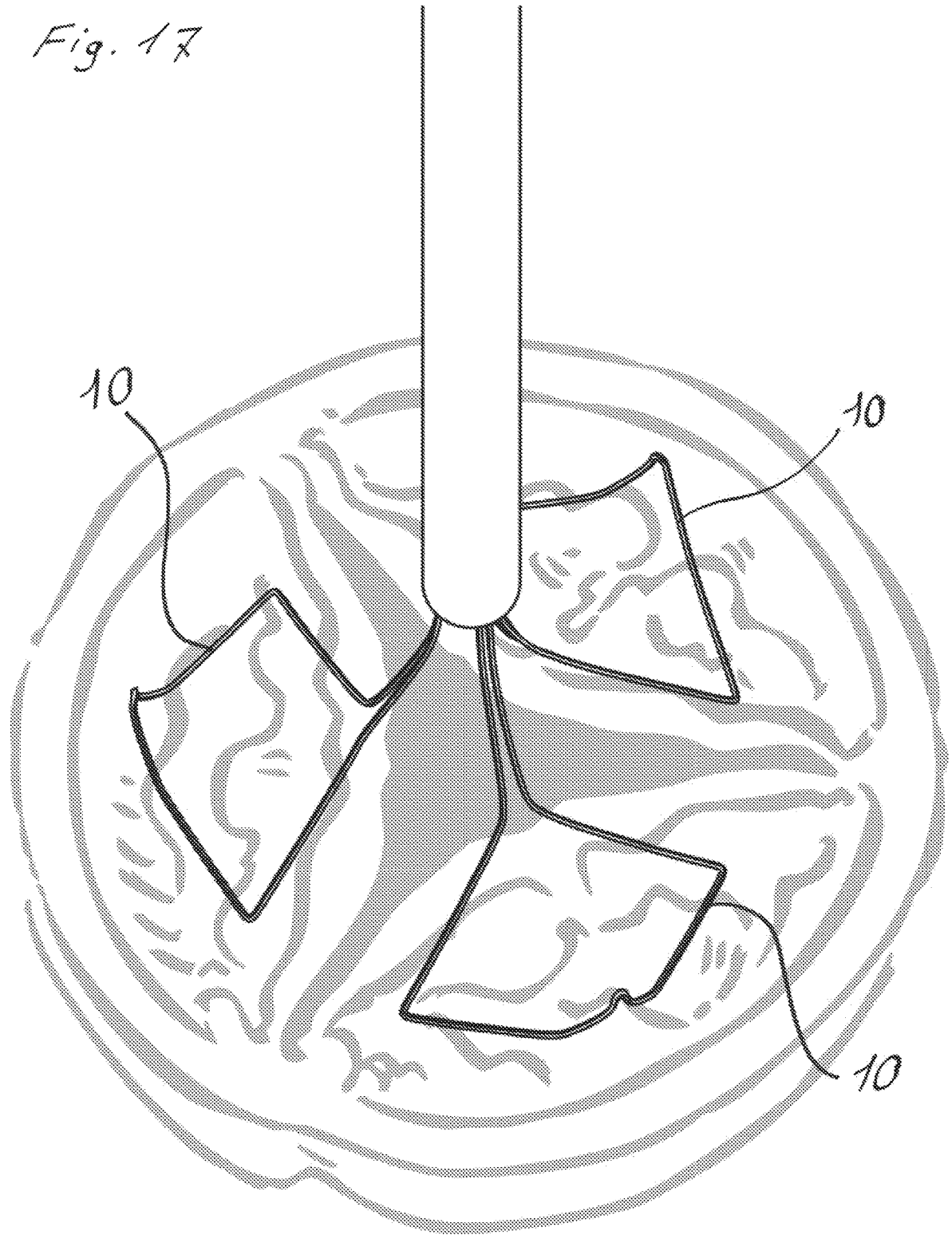
Figure 18:
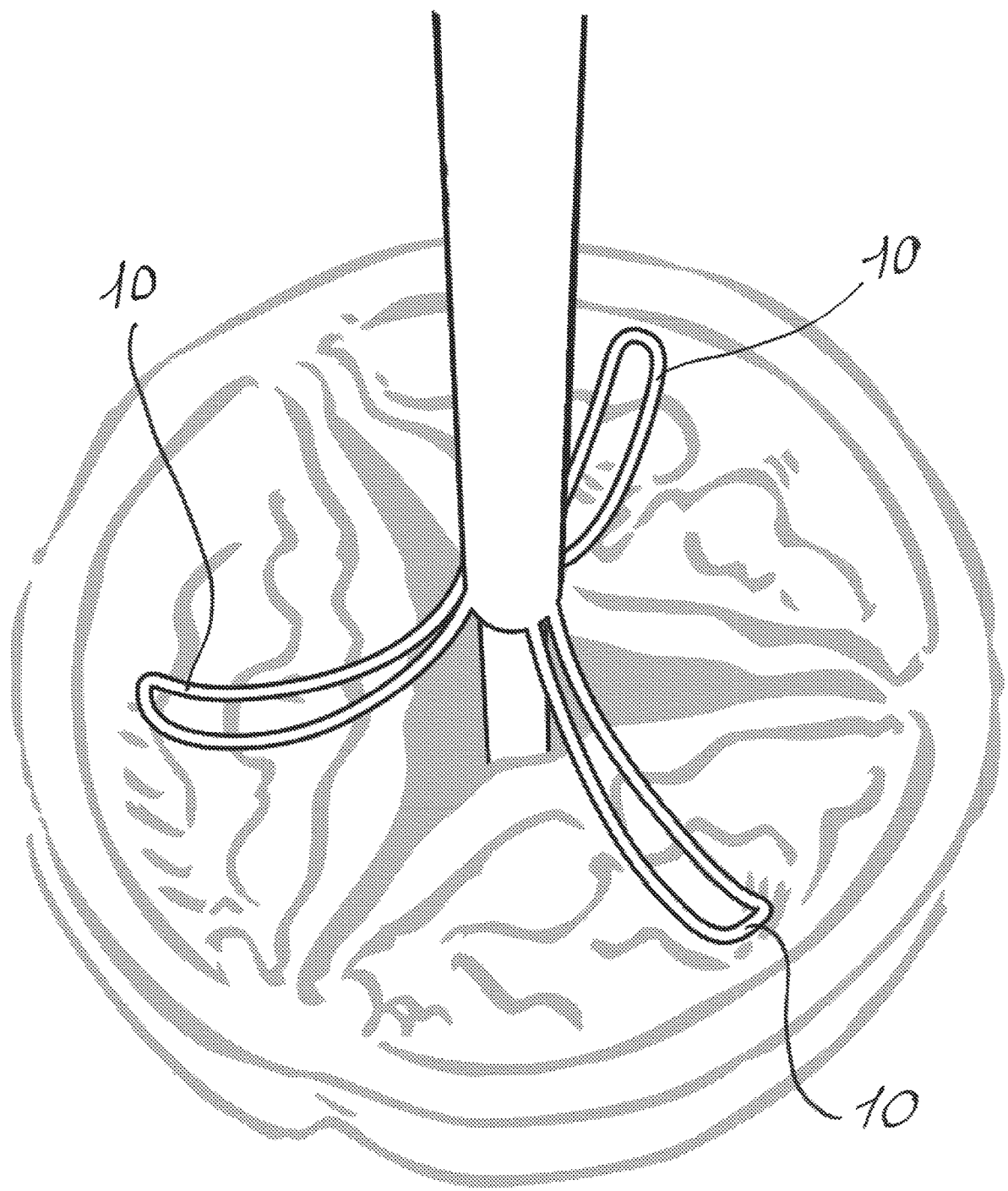
Figure 19:
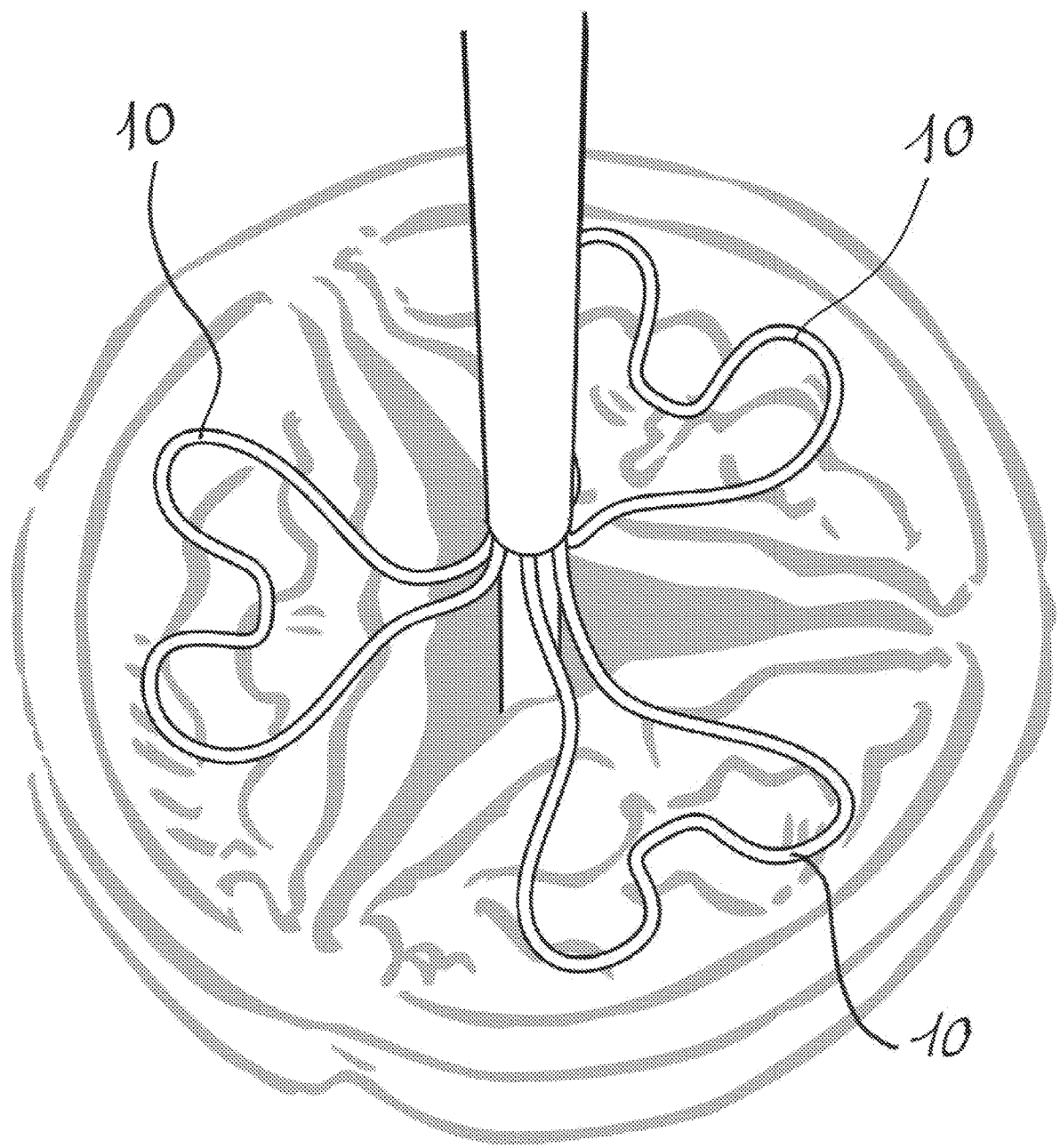
Figure 20:
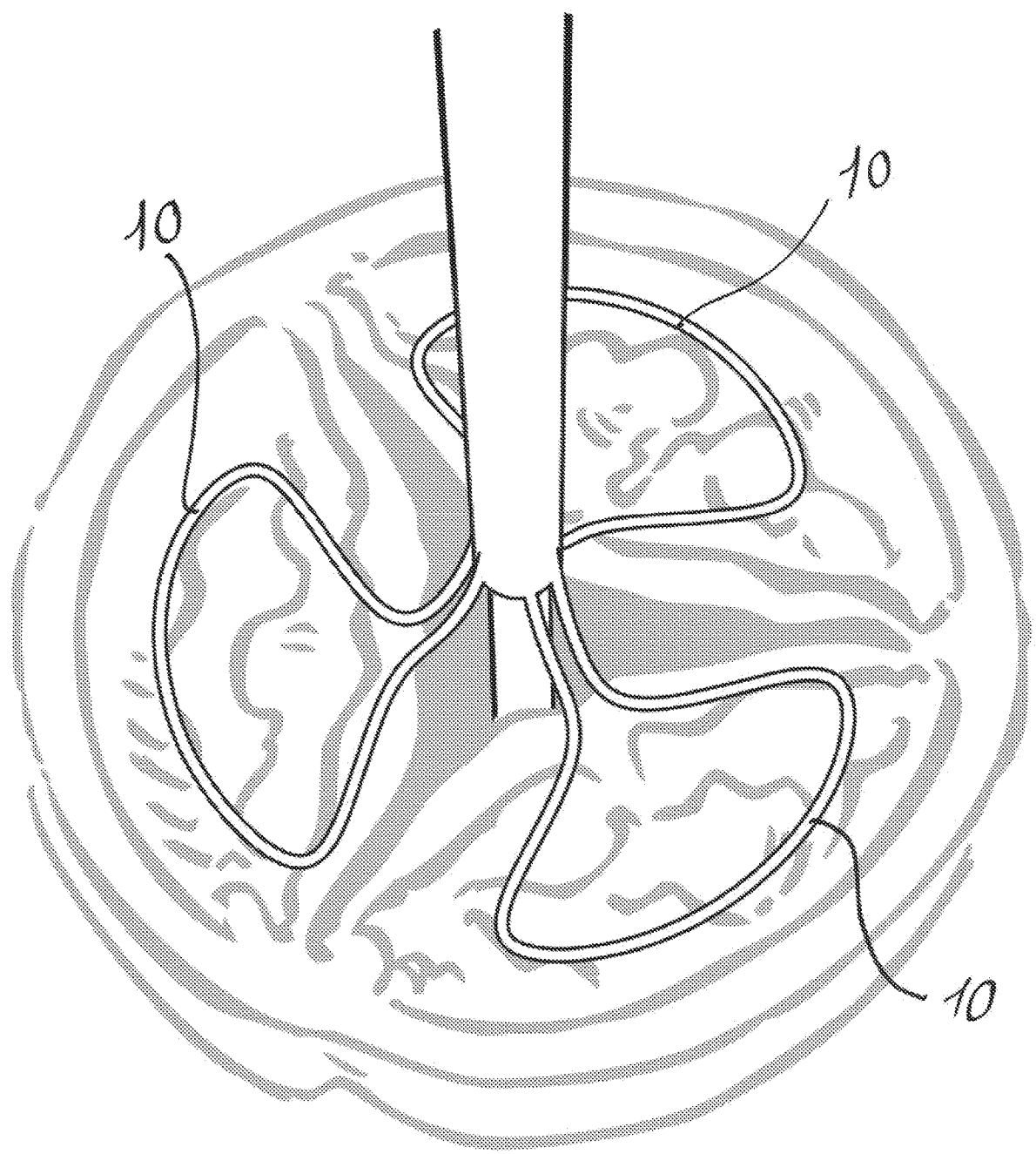

In FIG. 12 an example of three aortic leaflet debriders 9 with the geometry of the debrider arms 10 are represented. In this embodiment, the three aortic leaflet debriders 9 are shaped in a way to adapt into the belly of each aortic leaflet. They are characterized by debrider arms 10 carrying on a certain number of piezoelectric elements 11. The debrider arms 10 can be a wire but, as described in the present embodiment is a flexible metal pipe (stainless steel, Nitinol, et.) that be drilled with micro-holes 12 aimed at distributing $CO_2$ so that obtaining a potentiation of the cavitation effect, as previously described. In addition, the operator can apply, to the aortic leaflet debriders 9, a swirling action (FIG. 21) in order to cover a larger leaflets' surface getting therefore a better effect.

In figures from 13 to 20 other different embodiments about different geometric configurations of the aortic leaflet debriders 9 are represented.

Figure 22:
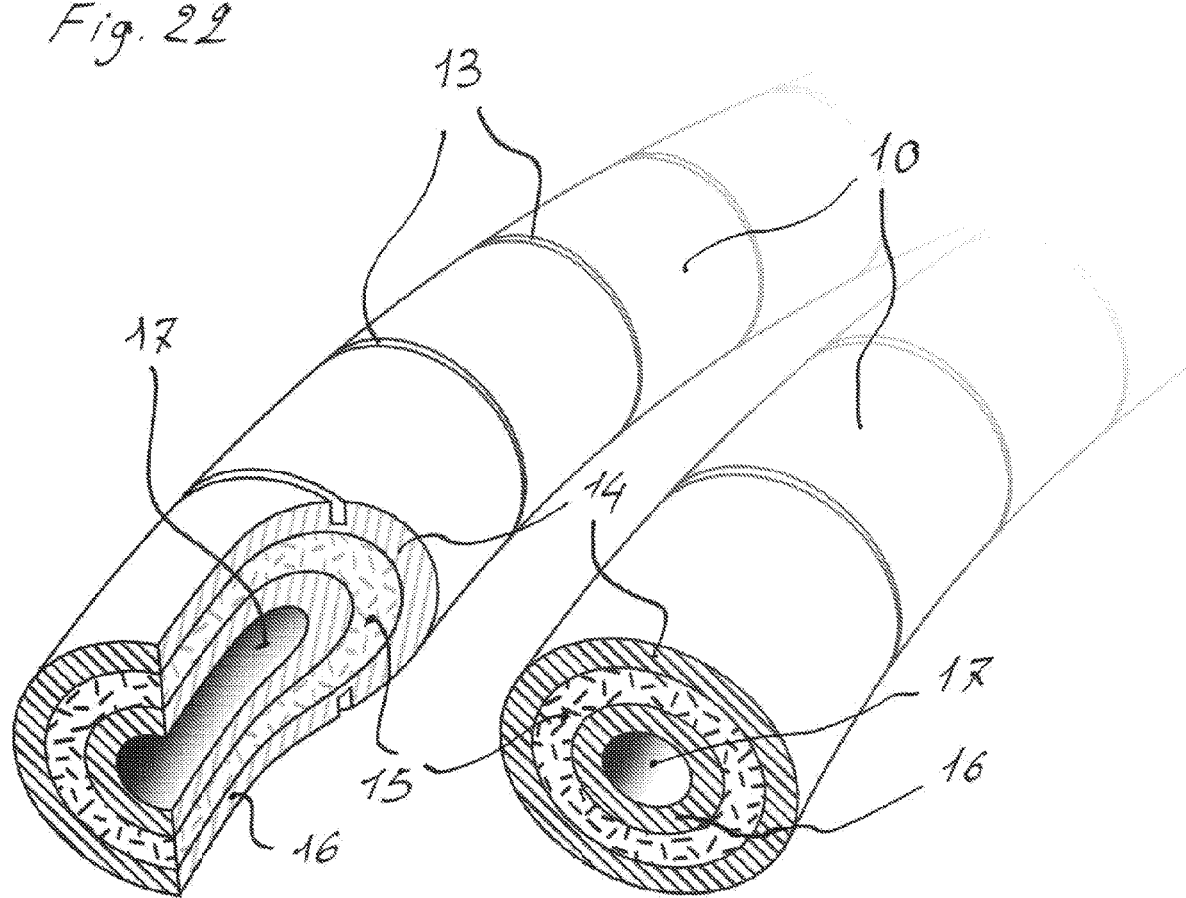
FIG. 22: Two coaxial pipes (external pipe 14 and internal pipe 16) characterize the structure of the debrider arms 10. A piezoelectric material 15 fills the intermediate space. This piezoelectric material 15 can be solid like a ceramic or a polymer like PVDF (Polyvinylidene fluoride). Inside the lumen 17 can circulate a cooling liquid (e.g. cold water) or a cooling gas (e.g. $CO_2$) avoiding, if needed, an excessive increase of temperature during the procedure.
Figure 23:
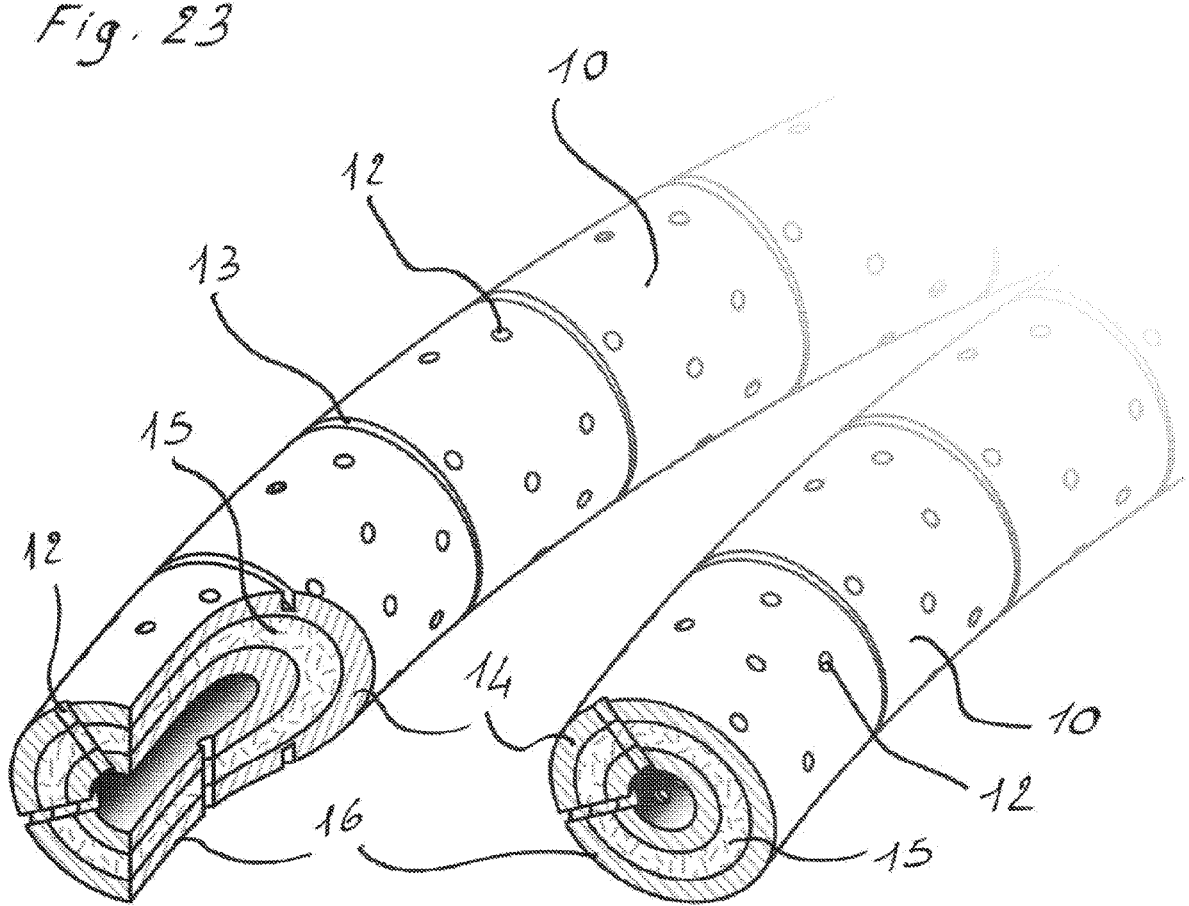
FIG. 23: As reported in FIG. 22 but the debrider arms 10 despite preserving the same structure above described are showing a series of micro-holes 12 drilled on the surface. The scope of these micro-holes 12 is to allow the injection of $CO_2$ gas with the goal to enhance the cavitation mechanism.

The debrider arms 10 described in all above geometrical configurations can be realized, in a further embodiment, with a coaxial geometry as represented in FIGS. 22 and 23.

Two coaxial pipes characterize the structure of this debrider arm 10. The external pipe 14 (stainless steel, Nitinol, conductive polymers with nano-tubes, etc.) carries circumferential micro-incisions 13, not passing through the entire pipe thickness, aimed at providing the necessary flexibility. These micro-incisions 13 can be applied in all variable embodiments such as, for example, not covering the entire circumference, varying the distance among them, etc. The coaxial inner pipe 16 (stainless steel, Nitinol, conductive polymers with nano-tubes, etc.) creates a space gap with the outer pipe 14 so that in this embodiment can be filled in with a piezoelectric material 15 (FIG. 22). This piezoelectric material 15 can be solid like a ceramic or a polymer like PVDF (Polyvinylidene fluoride). A strong vibration induced by the piezoelectric material 15 induces the debridement action. The piezoelectric material is activated by the inner pipe 16 and the outer pipe 14 connected to an electric source. In the internal lumen 17, of the inner pipe 16, can circulate a cooling fluid in order to maintain low the temperature during the procedure. In another embodiment showed in FIG. 23 the debrider arms 10 are drilled with a number of micro-holes 12 aimed at distributing $CO_2$ to potentiate the cavitation effect.

Figure 24:
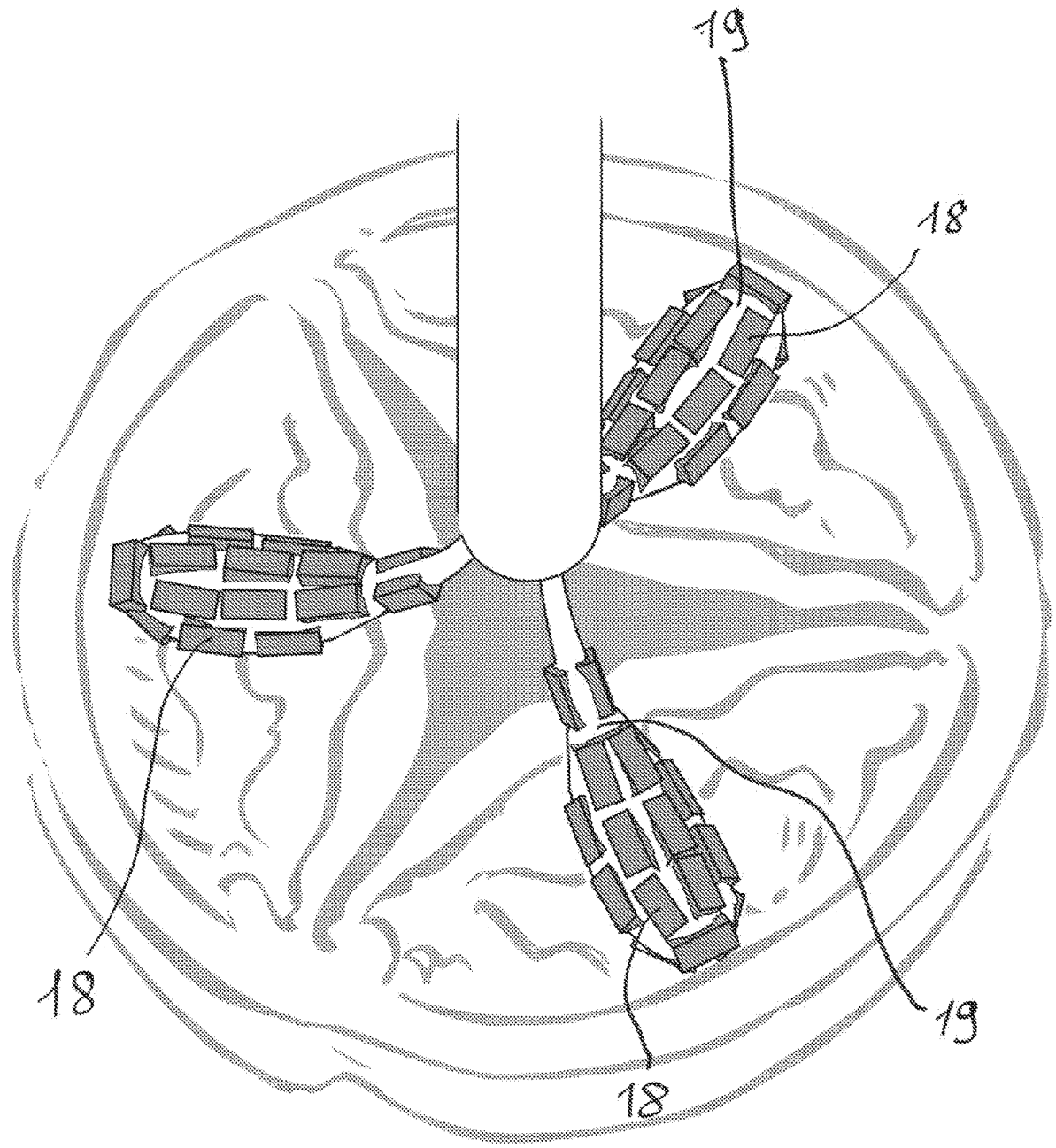
FIG. 24: In another embodiment, the debridement arms 10 can be realized with piezoelectric elements 18 mounted on a debridement's balloon 19. Here in the picture the balloon is represented in deflated configuration.
Figure 25:
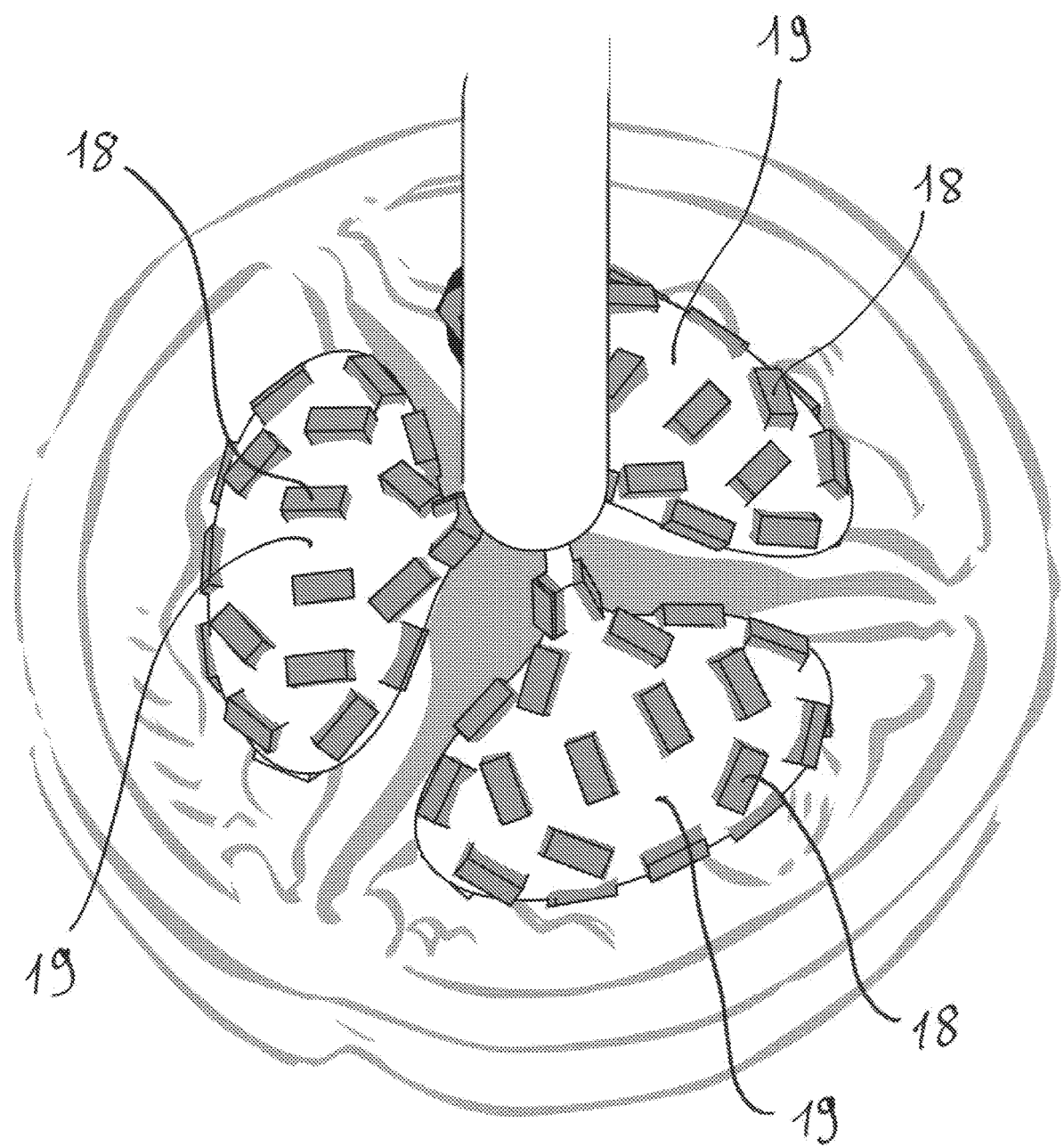
FIG. 25: The same as the FIG. 24 but the debrider balloon 19 is inflated with radiopaque medium. In this configuration, the piezoelectric elements are coming better in contact with the calcific tissues of the leaflet's belly.

The debridement action on the native aortic valve can be obtained in a further different way making the aortic leaflet debriders 9 in shape of balloon fitting inside the aortic leaflet belly. The balloon debriders 19 are embedding in their wall micro-piezoelectric elements 18 with their relative electrical connections. This debridement solution is represented in FIGS. 23 and 24 in which, the debrider balloons are respectively in deflated and inflated condition. The debrider balloons 19 can be inflated with simple cool saline or radiopaque medium in case X-ray visibility during the treatment procedure is required.

The invention claimed is:

1. A transcatheter device for a treatment of calcified native heart valve leaflets, the transcatheter device comprising:
   an outer hollow shaft;
   an inner hollow shaft slidingly arranged within the outer shaft;
   an axle body slidingly arranged within the inner shaft;
   a commissure debridement system located at a distal end of the axle body made of at least two radially expandable arms that are configured to be inserted in and aligned with native commissures; and
   leaflet debriders slidingly arranged between the outer hollow shaft and the inner hollow shaft, the leaflet debriders being radially expandable and configured to be positioned on each side of the leaflets.

2. The transcatheter device according to claim 1, wherein the at least two radially expandable arms include three expandable arms forming an angle of 120° between each other in an expanded state.

3. The transcatheter device of claim 1, further comprising:
   leaflet supports slidingly arranged between the outer shaft and the inner shaft, the leaflet supports being radially expandable and configured to be positioned on each side of the leaflets at a ventricle side.

4. A transcatheter device for a treatment of calcified native heart valve leaflets, the transcatheter device comprising:
   an outer hollow shaft;
   an inner hollow shaft slidingly arranged within the outer shaft;
   an axle body slidingly arranged within the inner shaft;
   a commissure debridement system located at a distal end of the axle body made of at least two radially expandable arms that are configured to be inserted in and aligned with native commissures; and
   leaflet supports and leaflet debriders that are slidingly arranged between the outer shaft and the inner shaft, the leaflet supports and the leaflet debriders being radially expandable and configured to be positioned on each side of the leaflets.

5. The transcatheter device according to claim 4, wherein each one of the leaflet debriders includes a vibrating device.

6. The transcatheter device according to claim 5, wherein the vibrating device includes a piezo-electric element.

7. The transcatheter device according to claim 4, wherein the leaflet debriders include a plurality of arms, each of the arms forming a closed loop.

* * * * *